(12) United States Patent
Phiasivongsa et al.

(10) Patent No.: US 10,301,287 B2
(45) Date of Patent: May 28, 2019

(54) SOLID FORMS OF CENICRIVIROC MESYLATE AND PROCESSES OF MAKING SOLID FORMS OF CENICRIVIROC MESYLATE

(71) Applicant: Tobira Therapeutics, Inc., Parsippany, NJ (US)

(72) Inventors: Pasit Phiasivongsa, South San Francisco, CA (US); Martin Ian Cooper, Cambridge (GB); Emma Kay Sharp, Cambridge (GB)

(73) Assignee: Tobira Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/691,191

(22) Filed: Aug. 30, 2017

(65) Prior Publication Data
US 2018/0057481 A1 Mar. 1, 2018

Related U.S. Application Data

(60) Provisional application No. 62/382,153, filed on Aug. 31, 2016.

(51) Int. Cl.
*C07D 403/12* (2006.01)
*C07C 309/04* (2006.01)

(52) U.S. Cl.
CPC .......... *C07D 403/12* (2013.01); *C07C 309/04* (2013.01); *C07B 2200/13* (2013.01)

(58) Field of Classification Search
CPC .................................................. C07D 403/12
See application file for complete search history.

(56) References Cited

U.S. PATENT DOCUMENTS

| 7,371,772 | B2 | 5/2008 | Shiraishi et al. | |
|---|---|---|---|---|
| 8,183,273 | B2 * | 5/2012 | Shiraishi .............. | C07D 225/06 514/383 |
| 8,362,058 | B2 | 1/2013 | Shiraishi et al. | |
| 8,741,943 | B2 | 6/2014 | Shiraishi et al. | |
| 2004/0259876 | A1 | 12/2004 | Shiraishi et al. | |
| 2005/0107606 | A1 | 5/2005 | Tawada et al. | |
| 2006/0257403 | A1 | 11/2006 | Young et al. | |
| 2008/0161287 | A1 | 7/2008 | Shiraishi et al. | |
| 2008/0249147 | A1 | 10/2008 | Yoshinari | |
| 2009/0030032 | A1 | 1/2009 | Shiraishi et al. | |
| 2012/0232028 | A1 | 9/2012 | Shiraishi et al. | |
| 2016/0008326 | A1 | 1/2016 | Shiraishi et al. | |
| 2016/0081985 | A1 | 3/2016 | Menning et al. | |

FOREIGN PATENT DOCUMENTS

| EP | 1889839 A1 | 2/2008 |
|---|---|---|
| JP | 62-265270 A | 11/1987 |
| WO | WO 1996/001267 A1 | 1/1996 |
| WO | WO 1999/032100 A2 | 7/1999 |
| WO | WO 2000/010965 A2 | 3/2000 |
| WO | WO 2001/017947 A1 | 3/2001 |
| WO | WO 2003/014105 A1 | 2/2003 |
| WO | WO 2003/076411 A1 | 9/2003 |
| WO | WO 2012/068366 A2 | 5/2012 |
| WO | WO 2013/167743 A1 | 11/2013 |
| WO | WO 2015/143367 A2 | 9/2015 |
| WO | WO 2015/187663 A1 | 12/2015 |
| WO | WO 2016/105527 A1 | 6/2016 |

OTHER PUBLICATIONS

PCT/JP2002/008043, International Search Report dated Nov. 11, 2002, 4 pages.
PCT/JP2002/008043, International Preliminary Examination Report dated Nov. 7, 2003, 38 pages.
PCT/US2015/000289, International Search Report and Written Opinion dated Apr. 12, 2016, 16 pages.
PCT/US2015/000289, International Preliminary Report on Patentability dated Jun. 27, 2017, 12 pages.
PCT/US2017/049400, International Search Report and Written Opinion dated Jan. 8, 2018, 11 pages.
Baba, M., et al., "A small-molecule, nonpeptide CCR5 antagonist with highly potent and selective anti-HIV-1 activity," Proc. Natl. Acad Sci. USA (1999); 96: 5698-5703.
Baba, M., et al., "TAK-652 Inhibits CCR5-Mediated Human Immunodeficiency Virus Type 1 Infection In Vitro and Has Favorable Pharmacokinetics in Humans," Antimicrobial Agents and Chemotherapy (2005); 49(11): 4584-4591.
Dawson, T. C., et al. "Absence of CC chemokine receptor-2 reduces atherosclerosis in apolipoprotein E-deficient mice," Atherosclerosis (1999); 143: 205-211.
Carr, R.L., "Evaluating Flow Properties of Solids." Chem Eng (1965); 72: 163-168.
Fischereder, M., et al., "CC chemokine receptor 5 and renal-transplant survival," The Lancet (2001); 357: 1758-1761.
Fukushi et al., "Synthesis and Platelet-Activating Factor (PAF)—Antagonistic Activities of 1,4-Disubstituted Piperazine Derivatives," Chem. Pharm. Bull. (1994); 42(3): 541-550.
Horuk, R., "Chemokine receptors," Cytokine and Growth Factor Reviews (2001); 12(4): 313-335.
Kazmierski, W., et al., "Recent Progress in Discovery of Small-Molecule CCR5 Chemokine Receptor Ligands as HIV-1 Inhibitors," Bioorganic & Medicinal Chemistry (2003), 11: 2663-2676.
Liu, R., et al., "Homozygous Defect in HIV-1 Coreceptor Accounts for Resistance of Some Multiply-Exposed Individuals to HIV-1 Infection," Cell (1996); 86: 367-377.
Maeda, K., et al. "The current status of and challenges in the development of CCR5 inhibitors as therapeutics for HIV-1 infection," Current Opinion in Pharmacology (2004); 4(5): 447-452.

(Continued)

*Primary Examiner* — Paul V Ward

(74) *Attorney, Agent, or Firm* — Mintz Levin Cohn Ferris Glovsky and Popeo, P.C.

(57) ABSTRACT

The invention relates to solid forms of cenicriviroc mesylate, methods of their preparation, pharmaceutical compositions thereof and methods of their use.

44 Claims, 13 Drawing Sheets

(56) References Cited

OTHER PUBLICATIONS

Figure 1:
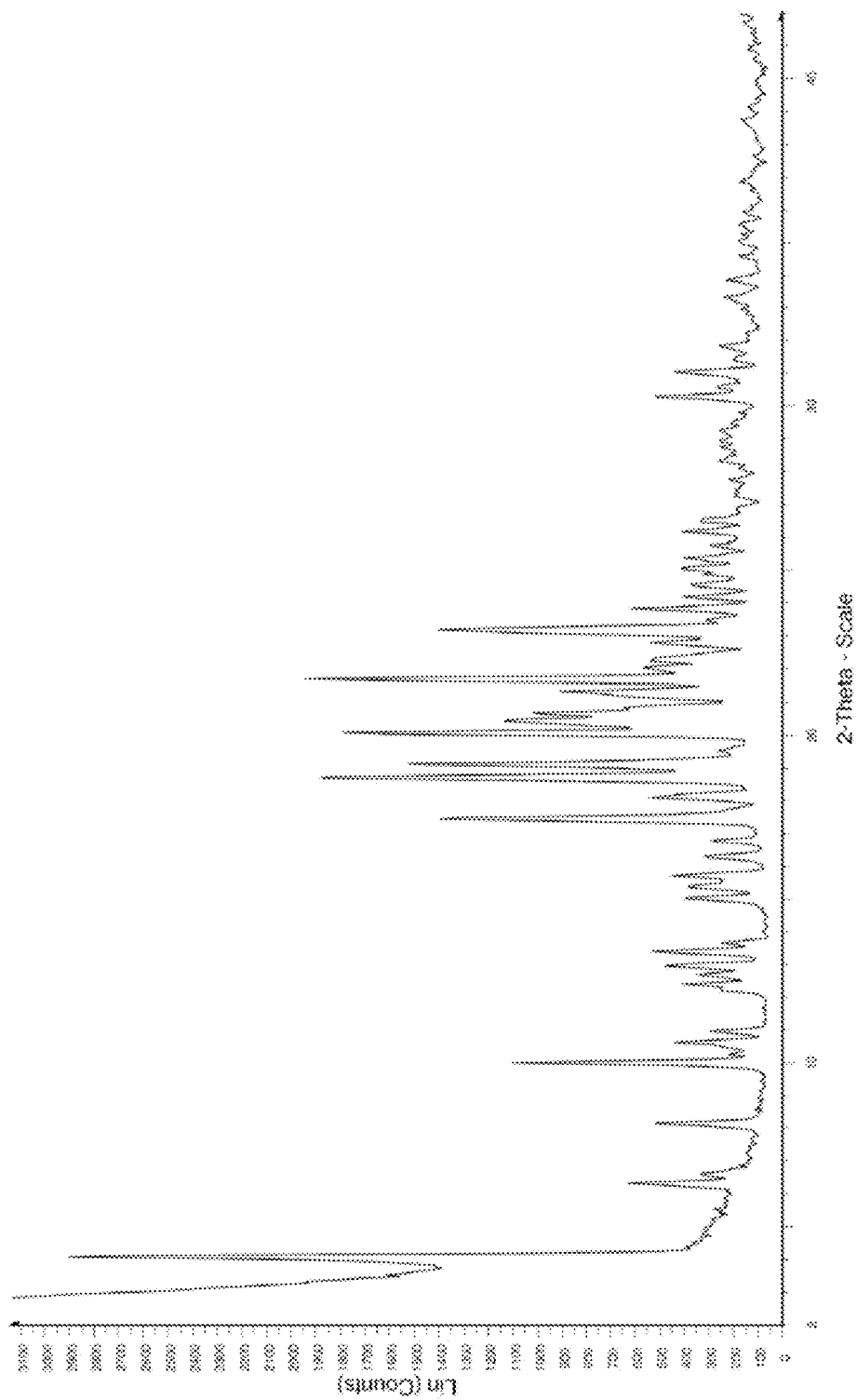

Pokorny, V., et al., "Evidence for negative association of the chemokine receptor CCR5 d32 polymorphism with rheumatoid arthritis," Ann. Rheum. Dis. (2005); 64: 487-490.

Princen, K. et al. "HIV chemokine receptor inhibitors as novel anti-HIV drugs", Cytokine & Growth Factor Reviews (2005); 16: 659-677.

Salmas et al., "Investigation of Inhibition Mechanism of Chemokine Receptor CCR5 by Micro-second Molecular Dynamics Simulations." Scientific Reports (2015); 5: 13180.

Samson, M., et al., "Resistance to HIV-I infection in caucasian individuals bearing mutant alleles ot he CCR-5 chemokine receptor gene," Nature (1996); 382: 722-725.

Sellebjerg, F. et al. "CCR5 Δ32, matrix metalloproteinase-9 and disease activity in multiple sclerosis", Journal of Neuroimmunology (2000); 102(1): 98-106.

Seto, M., et al., "Orally active CCR5 antagonists as anti-HIV-1 agents: synthesis and biological activity of 1-benzothiepine 1,1-dioxide and 1-benzazepine derivatives containing a tertiary amine moiety." Chem Pharm Bull (Tokyo) (2004); 52(5): 577-590.

Seto, M., et al., "Highly Potent and Orally Active CCR5 Antagonists as Anti-HIV-1 Agents: Synthesis and Biological Activities of 1-Benzazocine Derivatives Containing a Sulfoxide Moiety." J. Med. Chem. (2006); 49 (6): 2037-2048.

University of North Carolina School of Medicine, "Case of the Missing Monocyte: Gene Appears to Protect Against Rheumatoid Arthritis," ScienceDaily LLC, United States, Oct. 11, 2011, 3 pages.

Xia et al., "Recent Developments in CCR2 Antagonists." Expert Opinion on Therapeutic Patents (2009); 19(3): 295-303.

\* cited by examiner

SOLID FORMS OF CENICRIVIROC MESYLATE AND PROCESSES OF MAKING SOLID FORMS OF CENICRIVIROC MESYLATE

CROSS-REFERENCE TO RELATED APPLICATIONS

This application claims the benefit of priority to U.S. Provisional Patent Application No. 62/382,153 filed Aug. 31, 2016, the disclosure of which is hereby incorporated by reference in its entirety for all purposes.

FIELD OF THE DISCLOSURE

The present disclosure relates to solid forms of cenicriviroc (CVC) mesylate and processes for preparing such solid forms.

BACKGROUND OF THE DISCLOSURE

Cenicriviroc is the common name of (S,E)-8-(4-(2-Butoxyethoxy)phenyl)-1-(2-methylpropyl)-N-(4-(((1-propyl-1H-imidazol-5-yl)methyl)sulfinyl)phenyl)-1,2,3,4-tetrahydrobenzo[b]azocine-5-carboxamide (CVC), the chemical structure of which appears below.

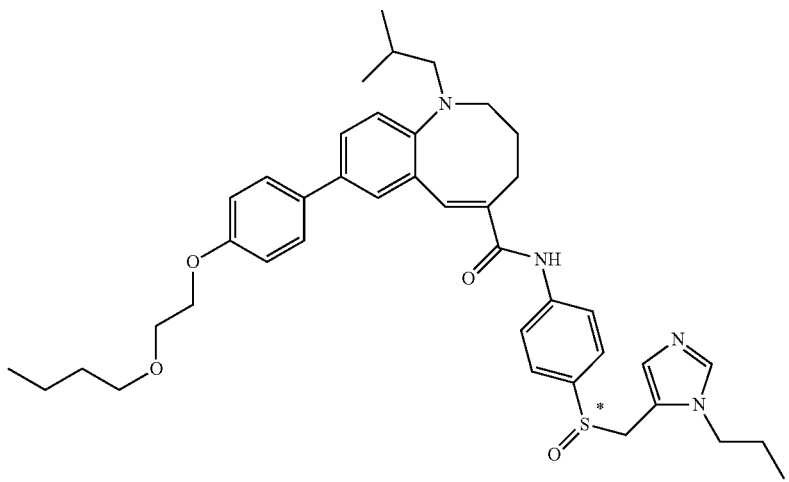

Cenicriviroc

Cenicriviroc binds to and inhibits the activity of the C—C chemokine receptor type 2 (CCR2) and C—C chemokine receptor type 5 (CCR5) receptors. These receptors not only play a role in entry of viruses such as Human Immunodeficiency Virus (HIV) into the cell, but also are important for the recruitment of immune cells to sites of injury. Inhibition of this receptor's activity may have an anti-inflammatory effect. Recently, the role that inflammation plays in the development of fibrosis has been examined. It has been shown that CCR2 and CCR5 may play a role in promoting hepatic fibrosis and that CVC has potential as a therapeutic agent in the treatment of hepatic fibrosis (International Publication No. WO 2015/143367).

The synthesis of CVC is described in U.S. Pat. No. 8,183,273; U.S. Publication No. 2005/0107606 and International Publication No. WO 2001/017947.

Cenicriviroc is weakly basic and poorly water-soluble. Several salts of CVC have been described. For example, U.S. Pat. No. 8,183,273; U.S. Publication No. 2005/107606 and International Publication No. WO 2016/105527 disclose preparations of a methanesulfonic acid salt of CVC (or CVC mesylate). However, none of these references describe a polymorphic form of the resulting CVC mesylate.

For instance, Example 10 of U.S. Pat. No. 8,183,273 discloses the preparation of "yellow crystals" of CVC mesylate. In the example, CVC (100 mg) was dissolved in ethyl acetate (4 mL) and methanesulfonic acid (9.31 µL in 2 mL of ethyl acetate) was added to the solution with vigorous stirring. After the addition was complete, the mixture was stirred overnight; the precipitated solids were collected by filtration; the collected solids were washed with ethyl acetate (5 mL) and dried under reduced pressure. The drying conditions (e.g., temperature, time and pressure) are not specified. The dried solids were recrystallized from 2-butanone (4 mL) to provide CVC mesylate as "yellow crystals." Neither the recrystallization temperature profile nor the conditions used to dry the CVC mesylate are described. The "yellow crystals" exhibited a melting point of 145.5-147.5° C. However, no other polymorphic form characteristics of the product are disclosed.

Examples 15, 16 and 19 from U.S. Publication No. 2005/107606 describe the preparation of CVC mesylate. The CVC mesylate produced in Examples 15 and 19 is said to be in the form of "yellow crystals". However, no other polymorphic form characteristics of the product are disclosed. Similarly, Example 16 is said to yield a "yellow powder". However, no other polymorphic form characteristics of the product are disclosed.

In Example 15, crude CVC was dissolved in a mixture of acetonitrile (7 mL) and acetone (7 mL), and methanesulfonic acid (209 mg) and "seed crystals" were successively added to the solution. The resulting mixture was stirred for 100 minutes after which time acetonitrile/acetone (1:1, 5.0 mL) was added; the mixture was further stirred at room temperature overnight and then stirred under ice-cooling for 2.5 h; the precipitated solids were collected by filtration and washed with ice-cooled acetone (9 mL). The collected solids were dried at 40° C. under reduced pressure to obtain CVC mesylate as "yellow crystals." Furthermore, the drying time for the "yellow crystals" is not described. Also, no other polymorphic form characteristics of the product are disclosed.

In Example 19, methanesulfonic acid (18.2 g) was added to a solution of crude CVC in a mixture of acetonitrile (720 mL) and ethyl acetate (720 mL), and the resulting mixture was stirred for 1 h after which time the precipitated solids were collected by filtration to provide CVC mesylate (141.8 g) as "yellow crystals." No physical form characterization data is provided for the "yellow crystals." Furthermore, the drying conditions (e.g., temperature, time and pressure) are not specified. Also, no other polymorphic form characteristics of the product are disclosed In Example 16, methanesulfonic acid (0.65 mL) and "seed crystals" (80 mg) were successively added to a solution of crude CVC in methyl isobutyl ketone (15 mL). The resulting mixture was stirred for 16 h after which time methyl isobutyl ketone/ethyl acetate (1:1, 50 mL) was added. The mixture was stirred under ice-cooling for 2 h; the precipitated solids were collected by filtration; and the collected solids were dried at 40° C. under reduced pressure to obtain CVC mesylate (6.62 g) as "yellow powder." The "yellow powder" was suspended in methyl isobutyl ketone (40 mL); the suspension was stirred for 16 hours; ethyl acetate (40 mL) was added to the suspension to provide a solution; the solution was stirred at room temperature for 1 hour; then stirred for 2 hours under ice-cooling and CVC mesylate was collected by filtration. The conditions used to dry CVC mesylate are not specified. The CVC mesylate produced in the example is described as a "yellow powder". However, no other polymorphic form characteristics of the product are disclosed.

Example 4 of International Publication No. WO 2016/105527 describes the preparation of solid CVC mesylate. In the example, crude CVC was dissolved in a mixture of ethyl acetate and acetonitrile, then methanesulfonic acid (1.01 equivalent) and ethyl acetate were successively added to the solution. The resulting mixture was stirred for 30 minutes after which time the mixture was seeded with CVC mesylate and the mixture was stirred at 20° C. for 8 hours. The precipitated solids were collected by filtration and washed with chilled ethyl acetate. These "crude crystals" were dissolved in acetonitrile at 70° C. and the solution was cooled to 50-55° C. over 1 hour and seeded with CVC mesylate. The solution was stirred at 50-55° C. for 6 hours then cooled to 20° C. over 1 hour then stirred for 8 hours. The precipitated crystals were collected by filtration and washed twice with chilled acetonitrile to provide CVC mesylate. The reference describes the product as a "bright yellow solid". However, no other polymorphic form characteristics of the product are disclosed.

M. Menning and S. Dalziel, Mol. Pharmaceutics (10) 4005-4015, 4006, (2013) disclose a monomesylate salt in a solid form as being a highly stable non-hygroscopic crystalline solid with a high melting point at 153° C. However, no other polymorphic form characteristics of the product are disclosed.

Thus, while the aforesaid described methods of making solid CVC mesylate, however the polymorphic characterization of the solids is not established. There is a need for CVC mesylate having high polymorphic purity and processes for making the same.

The present disclosure relates to polymorphic and stable amorphous forms of CVC mesylate, methods of their preparation, pharmaceutical compositions thereof and methods of their use.

SUMMARY OF THE DISCLOSURE

This disclosure relates to solid forms of a methanesulfonic acid salt of CVC (also "Compound I-MsOH" and "CVC mesylate") and methods of making such forms. In one embodiment, the solid forms are crystalline forms.

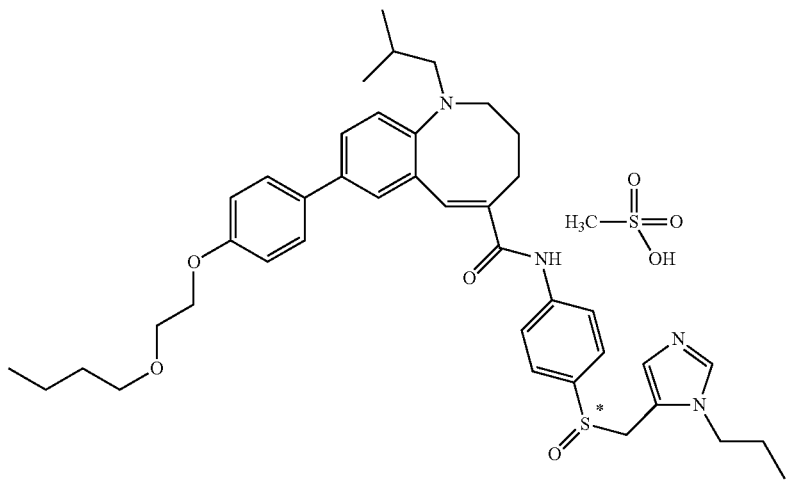

Compound I—MsOH

In some embodiments, the crystalline form of Compound I-MsOH is Crystalline Form A. In one embodiment, the Crystalline Form A exhibits an X-ray powder diffraction pattern comprising one or more peaks at about 4.0±0.2, about 18.7±0.2, about 19.1±0.2, about 20.1±0.2 and about 21.7±0.2 degrees two-theta. In another embodiment, the Crystalline Form A further exhibits one or more X-ray powder diffraction peaks at about 10.0±0.2, about 17.4±0.2, about 20.4±0.2, about 20.7±0.2, and about 23.2±0.2 degrees two-theta.

In one embodiment, the Crystalline Form A exhibits a differential scanning calorimetry thermogram having a peak characteristic value at about 152.9±2.0° C. In another embodiment, the Crystalline Form A exhibits a differential scanning calorimetry thermogram pattern substantially similar to FIG. 2. In one embodiment, the Crystalline Form A exhibits a thermogravimetric analysis thermogram substantially similar to FIG. 3.

In further embodiments, the Crystalline Form A is in a substantially pure form. In one embodiment, the Crystalline Form A has a polymorphic purity of at least about 50%. In another embodiment, the Crystalline Form A has a polymorphic purity of at least about 60%. In one embodiment, the Crystalline Form A has a polymorphic purity of at least about 70%. In another embodiment, the Crystalline Form A has a polymorphic purity of at least about 80%. In one embodiment, the Crystalline Form A has a polymorphic purity of at least about 90%. In another embodiment, the Crystalline Form A has a polymorphic purity of at least about 95%.

In one embodiment, the Crystalline Form A has a $D_{90}$ ranging from about 5 µm to about 10 µm. In one embodiment, the Crystalline Form A is micronized.

In other embodiments, the present disclosure provides a pharmaceutical composition comprising the Crystalline Form A and a pharmaceutically acceptable excipient.

In some embodiments, the crystalline form of Compound I-MsOH is Crystalline Form B. In one embodiment, the Crystalline Form B exhibits an X-ray powder diffraction pattern comprising one or more peaks at about 4.0±0.2, about 15.9±0.2, about 17.8±0.2, about 19.9±0.2, about 20.1±0.2, about 21.5±0.2 and about 21.6±0.2 degrees two-theta. In another embodiment, the Crystalline Form B further exhibits X-ray powder diffraction pattern comprises one or more peaks at about 6.3±0.2, about 9.9±0.2, about 18.6±0.2, about 20.4±0.2 and about 21.1±0.2 degrees two-theta.

In further embodiments, the Crystalline Form B is in a substantially pure form. In one embodiment, the Crystalline Form B has a polymorphic purity of at least about 50%. In another embodiment, the Crystalline Form B has a polymorphic purity of at least about 60%. In one embodiment, the Crystalline Form B has a polymorphic purity of at least about 70%. In another embodiment, the Crystalline Form B has a polymorphic purity of at least about 80%. In one embodiment, the Crystalline Form B has a polymorphic purity of at least about 90%. In another embodiment, the Crystalline Form B has a polymorphic purity of at least about 95%.

In one embodiment, the Crystalline Form B has a $D_{90}$ ranging from about 5 µm to about 10 µm.

In other embodiments, the present disclosure provides a pharmaceutical composition comprising the Crystalline Form B and a pharmaceutically acceptable excipient.

In some embodiments, the solid form of Compound I-MsOH is Crystalline Form C. In one embodiment, the Crystalline Form C exhibits an X-ray powder diffraction pattern comprising one or more peaks at about 4.0±0.2, about 10.0±0.2, about 16.0±0.2, about 18.7±0.2, about 20.0±0.2 and about 21.7±0.2 degrees two-theta. In another embodiment, the Crystalline Form C further exhibits X-ray powder diffraction pattern comprises one or more peaks at about 17.4±0.2, about 20.3±0.2, about 20.6±0.2, about 20.7±0.2 and about 21.2±0.2 degrees two-theta.

Figure 7:
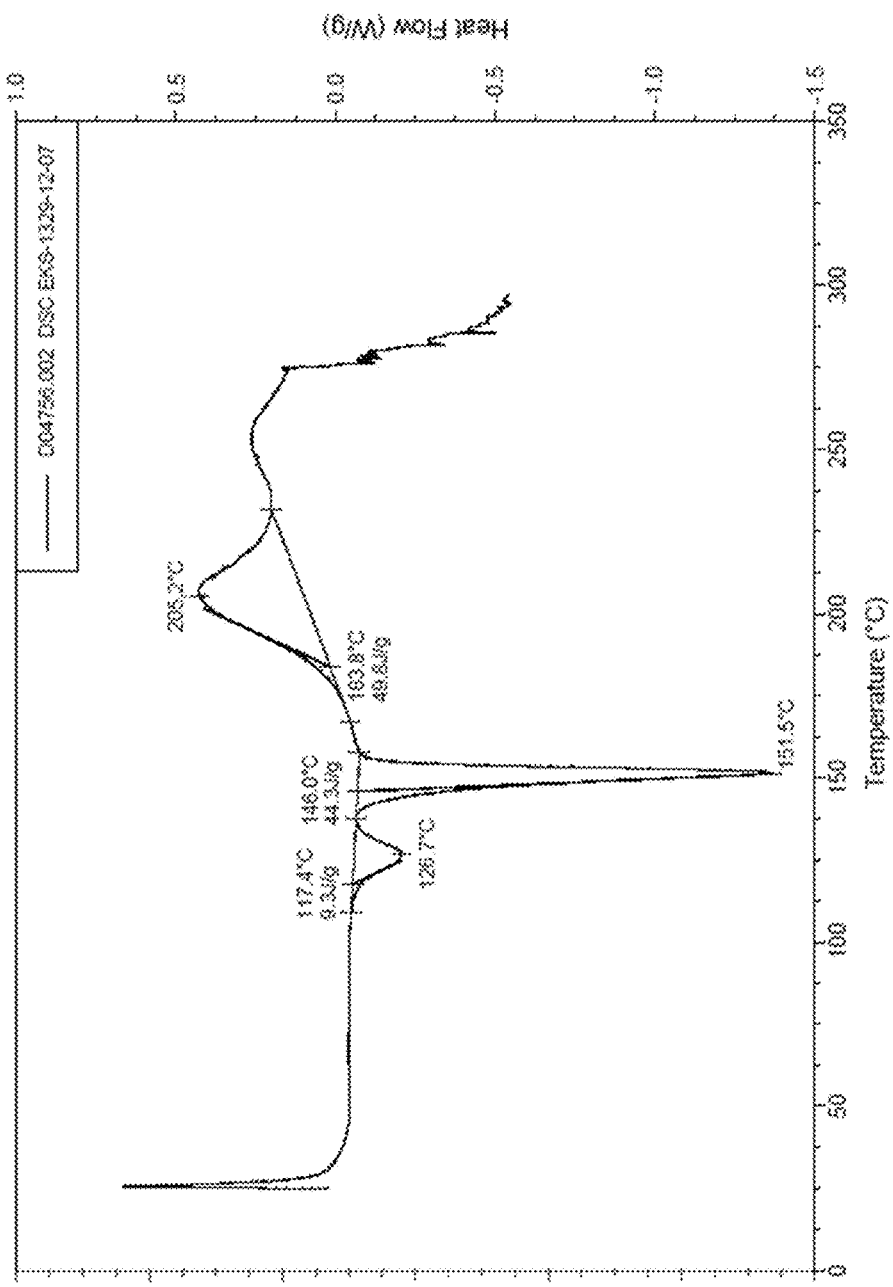
Figure 8:
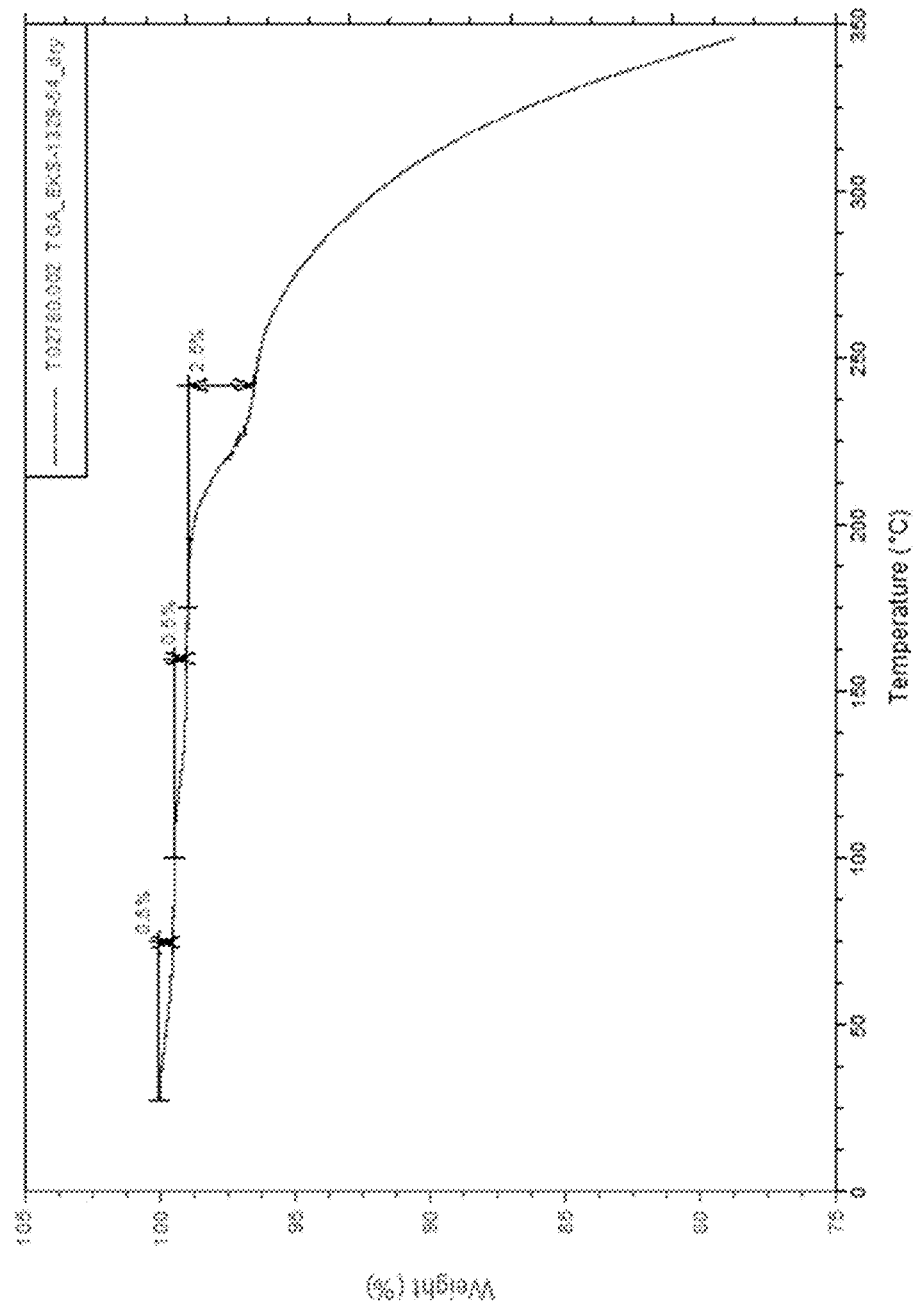

In one embodiment, the Crystalline Form C exhibits a thermogravimetric analysis thermogram substantially similar to FIG. 8. In another embodiment, the Crystalline Form C exhibits a differential scanning calorimetry thermogram having peak characteristic values at about 126.7±2.0 and about 151.5±2.0° C. In other embodiments, the Crystalline Form C exhibits a differential scanning calorimetry thermogram pattern substantially similar to FIG. 7.

In further embodiments, the Crystalline Form C is in a substantially pure form. In one embodiment, the Crystalline Form C has a polymorphic purity of at least about 50%. In another embodiment, the Crystalline Form C has a polymorphic purity of at least about 60%. In one embodiment, the Crystalline Form C has a polymorphic purity of at least about 70%. In another embodiment, the Crystalline Form C has a polymorphic purity of at least about 80%. In one embodiment, the Crystalline Form C has a polymorphic purity of at least about 90%. In another embodiment, the Crystalline Form C has a polymorphic purity of at least about 95%.

In one embodiment, the Crystalline Form C has a $D_{90}$ ranging from about 5 µm to about 10 µm.

In other embodiments, the present disclosure provides a pharmaceutical composition comprising the Crystalline Form C and a pharmaceutically acceptable excipient.

In some embodiments of the present disclosure, Compound I-MsOH has an amorphous form. In one embodiment, the amorphous form of Compound I-MsOH is stable. In another embodiment, the amorphous form of Compound I-MsOH exhibits a modulated DSC thermogram comprising a glass transition temperature at about 81.9° C. In other embodiments, the present disclosure provides a pharmaceutical composition comprising an amorphous form of Compound I-MsOH and a pharmaceutically acceptable excipient.

In other embodiments, methods of making Crystalline Form A of Compound I-MsOH are provided. In further embodiments, the Crystalline Form A produced by these methods is in a substantially pure form. In one embodiment, the method of making Crystalline Form A comprises: (a) suspending a Compound I-MsOH in a suitable solvent to form a slurry and (b) isolating Crystalline Form A of Compound I-MsOH. In one embodiment, the Compound I-MsOH in step (a) comprises amorphous Compound I-MsOH. In other embodiments, the suspending step (a) is conducted at about 5° C. and the solvent is selected from ethyl acetate, isopropyl acetate, methyl isobutyl ketone, isopropanol, ethanol, 2-methyl-1-propanol, propyl acetate, acetonitrile, 1,2-dimethoxyethane, nitromethane, ethyl acetate/acetonitrile (e.g., 50/50); ethyl acetate/acetonitrile/water (e.g., 47.5/47.5/5); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) or acetonitrile/dichloromethane (e.g., 95/5). In some embodiments, the suspending step (a) is conducted at a temperature of about 50° C. and the solvent is selected from ethyl acetate, isopropyl acetate, methyl isobutyl ketone, isopropanol, ethanol, 2-methyl-1-propanol, propyl acetate, acetonitrile, 1,2-dimethoxyethane, nitromethane, ethyl acetate/acetonitrile (e.g., 50/50); ethyl acetate/acetonitrile/water (e.g., 47.5/47.5/5); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) or acetonitrile/dichloromethane (e.g., 95/5).

In another embodiment, a method of making Crystalline Form A comprises: (a) suspending a Compound I-MsOH in a suitable solvent at a temperature of about 5° C.; (b) heating the suspension of step (a) to a temperature of about 50° C.; (c) isolating Crystalline Form A of Compound I-MsOH; and (d) drying the isolated product under vacuum, and breaking up product to dry at about 40° C. In one embodiment, the Compound I-MsOH in step (a) comprises an amorphous Compound I-MsOH. In one embodiment, the suitable solvent is selected from the group consisting of ethyl acetate, isopropyl acetate, methyl isobutyl ketone, isopropanol, methyl ethyl ketone, acetone, 2-methyl-1-propanol, tert-butyl methyl ether, anisole, toluene, tetrahydrofuran, acetonitrile, 1,2-dimethoxyethane, nitromethane, ethyl acetate/acetonitrile (e.g., 50/50); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) and acetonitrile/dichloromethane (e.g., 95/5).

In another embodiment, a method of making Crystalline Form A comprises: (a) suspending a Compound I-MsOH in a suitable solvent at a temperature of about 25° C.; (b) heating the suspension of step (a) to a temperature of about 50° C.; (c) isolating Crystalline Form A of Compound I-MsOH; and (d) drying the isolated product under vacuum, and breaking up product to dry at about 40° C. In one embodiment, the Compound I-MsOH in step (a) comprises an amorphous Compound I-MsOH. In one embodiment, the suitable solvent is selected from the group consisting of ethyl acetate, isopropyl acetate, methyl isobutyl ketone, isopropanol, methyl ethyl ketone, acetone, 2-methyl-1-propanol, tert-butyl methyl ether, anisole, toluene, tetrahydrofuran, acetonitrile, 1,2-dimethoxyethane, nitromethane, ethyl acetate/acetonitrile (e.g., 50/50); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) and acetonitrile/dichloromethane (e.g., 95/5).

In one embodiment, a method of making Crystalline Form A comprises: (a) adding an anti-solvent to a solution of a Compound I-MsOH in a suitable solvent to precipitate Crystalline Form A and (b) isolating Crystalline Form A of Compound I-MsOH. In one embodiment, the Compound I-MsOH in step (a) comprises an amorphous Compound I-MsOH. In some embodiments, the suitable solvent is methanol and the suitable anti-solvent is tert-butyl methyl ether. In other embodiments, the suitable solvent is ethanol:water (e.g., 90:10); and the suitable anti-solvent is tert-butyl methyl ether. In another embodiment, the suitable solvent is ethyl acetate:acetonitrile:water (e.g., 47.5:47.5:5); and the suitable anti-solvent is tert-butyl methyl ether. In some embodiments, the suitable solvent is methanol; and the suitable anti-solvent is tert-butyl methyl ether.

In another embodiment, a method of making Crystalline Form A comprises: (a) adding an anti-solvent to a solution of a Compound I-MsOH in a suitable solvent to form an oil that converts to Crystalline Form A and (b) isolating Crystalline Form A of Compound I-MsOH. In one embodiment, the Compound I-MsOH in step (a) comprises an amorphous Compound I-MsOH. In other embodiments, the suitable solvent is ethanol:water (e.g., 90:10); and the suitable anti-solvent is tert-butyl methyl ether. In another embodiment, the suitable solvent is ethyl acetate:acetonitrile:water (e.g., 47.5:47.5:5); and the suitable anti-solvent is tert-butyl methyl ether. In some embodiments, the suitable solvent is methanol; and the suitable anti-solvent is tert-butyl methyl ether.

In another embodiment, a method of making Crystalline Form A comprises: (a) dissolving a Compound I-MsOH in a suitable solvent; (b) evaporating a portion of the suitable solvent from the solution of step (a); and (c) evaporating a portion of the suitable solvent from the solution of step (a). In one embodiment, the Compound I-MsOH in step (a) comprises an amorphous Compound I-MsOH. In some embodiments, the suitable solvent is selected from the group consisting of anisole, 2-methyl-1-propanol and isopropanol/water (90:10).

In one embodiment, a method of making Crystalline Form A comprises: (a) suspending a Compound I-MsOH in a suitable solvent; (b) milling the suspension of step (a); and (c) isolating Crystalline Form A of Compound I-MsOH. In one embodiment, the Compound I-MsOH in step (a) comprises an amorphous Compound I-MsOH. In another embodiment, a ball mill is used in the milling step (b) and the suitable solvent is selected from the group consisting of isopropanol, acetone, ethanol, acetonitrile and nitromethane.

In other embodiments, methods of making Crystalline Form B are provided. In further embodiments, the Crystalline Form B produced by these methods is in a substantially pure form. In one embodiment, a method of making Crystalline Form B comprises: (a) suspending Compound I-MsOH in a suitable solvent and (b) forming a suspension of Crystalline Form B of Compound I-MsOH in the solvent. In one embodiment, the Compound I-MsOH in step (a) comprises an amorphous Compound I-MsOH. In some embodiments, the forming of the suspension of Crystalline Form B of Compound I-MsOH is at about 5° C. and the solvent is selected from methyl ethyl ketone, acetone and tetrahydrofuran. In other embodiments, the forming of the suspension of Crystalline Form B of Compound I-MsOH is at about 25° C. and the solvent is selected from acetone and tetrahydrofuran.

In one embodiment of the present disclosure, Crystalline Form A of Compound I-MsOH prepared by any one of the disclosed method as disclosed herein is provided.

In one embodiment, a method of making Crystalline Form B comprises: (a) dissolving a Compound I-MsOH in a suitable solvent; (b) adding a suitable anti-solvent to the solution of step (a); and (c) forming a suspension of Crystalline Form B of Compound I-MsOH. In one embodiment, the Compound I-MsOH in step (a) comprises an amorphous Compound I-MsOH. In some embodiments, the suspension of Crystalline Form B of Compound I-MsOH is formed at about 5° C. or at about 25° C., the suitable solvent is dichloromethane and the suitable anti-solvent is n-heptane.

In one embodiment of the present disclosure, Crystalline Form B of Compound I-MsOH prepared by any one of the disclosed method as disclosed herein is provided.

In other embodiments, methods of making Crystalline Form C are provided. In further embodiments, the Crystalline Form C produced by these methods is in a substantially pure form. In one embodiment, a method of making Crystalline Form C comprises: (a) filtering suspension of Crystalline Form B of Compound I-MsOH, and (b) drying the filtered product under vacuum, and breaking up product to dry at ambient conditions.

In another embodiment, a method of making Crystalline Form C comprises: (a) filtering suspension of Crystalline Form B of Compound I-MsOH, and (b) drying the filtered product under vacuum, and breaking up product to dry at less than about 20° C.

In one embodiment, a method of making Crystalline Form C comprises: (a) filtering suspension of Crystalline Form B of Compound I-MsOH, and (b) drying the filtered product under vacuum, and breaking up product to freeze-dry.

In one embodiment of the present disclosure, Crystalline Form C of Compound I-MsOH prepared by any one of the disclosed method as disclosed herein is provided.

In other embodiments, methods of making an amorphous form of Compound I-MsOH are provided. In other embodiments, methods of making a stable amorphous form of Compound I-MsOH are provided. In one embodiment, a method of making an amorphous Compound I-MsOH comprises: (a) dissolving a Compound I-MsOH in a suitable solvent; (b) evaporating a portion of the suitable solvent from the solution of step (a); and (c) isolating an amorphous form of Compound I-MsOH. In some embodiments, the suitable solvent is selected from the group consisting of dichloromethane, tetrahydrofuran and methanol. In another embodiment, the evaporating step (b) is conducted under ambient conditions. In one embodiment, the evaporating step (b) is conducted under pressure below that of atmospheric pressure.

In one embodiment, a method of making an amorphous Compound I-MsOH comprises: (a) dissolving a Compound I-MsOH in a suitable solvent; (b) freeze-drying the solution of step (a); and (c) isolating an amorphous form of Compound I-MsOH. In one embodiment, the suitable solvent is a mixture of tert-butanol and water.

In one embodiment of the present disclosure, an amorphous form of a Compound I-MsOH prepared by any one of the disclosed method as disclosed herein is provided.

In another embodiment, a method of administering a solid form of Compound I-MsOH is provided comprising administering a composition, formulation, tablet, or composition described by any of the above-mentioned embodiments. In another embodiment, a method of treating a disease, disorder, or condition is provided comprising administering a therapeutically effective amount of a composition, formulation, tablet, or composition produced by any of the above-mentioned embodiments. In further embodiments, the disease, disorder, or condition is a viral infection. In other further embodiments, the viral infection is a retroviral infection. In other further embodiments, the disease, condition, or disorder is hepatitis, human immunodeficiency virus, or a sarcoma virus. In certain embodiments, the disease, condition, or disorder is human immunodeficiency virus. In additional embodiments, the disease, disorder, or condition is inflammation. In further additional embodiments, the disease, disorder or condition is graft versus host disease, diabetic inflammation, cardiovascular inflammation, or fibrosis.

In one embodiment, the present disclosure provides a method of treating fibrosis or a fibrotic disease or condition in a subject in need thereof, comprising administering a therapeutically effective amount of any one of the Crystalline Form A of Compound I-MsOH as disclosed herein. In another embodiment, the present disclosure provides a method of treating fibrosis or a fibrotic disease or condition in a subject in need thereof, comprising administering a therapeutically effective amount of Crystalline Form B of Compound I-MsOH as disclosed herein. The present disclosure provides a method of treating fibrosis or a fibrotic disease or condition in a subject in need thereof, comprising administering a therapeutically effective amount of Crystalline Form C of Compound I-MsOH as disclosed herein. The present disclosure provides a method of treating fibrosis or a fibrotic disease or condition in a subject in need thereof, comprising administering a therapeutically effective amount of an amorphous form of Compound I-MsOH as disclosed herein. In one embodiment, the fibrosis or fibrotic disease or condition is liver fibrosis or renal fibrosis. In another embodiment, the liver fibrosis is associated with non-alcoholic steatohepatitis (NASH) or non-alcoholic fatty liver disease (NAFLD).

DETAILED DESCRIPTION OF THE DRAWINGS

Figure 2:
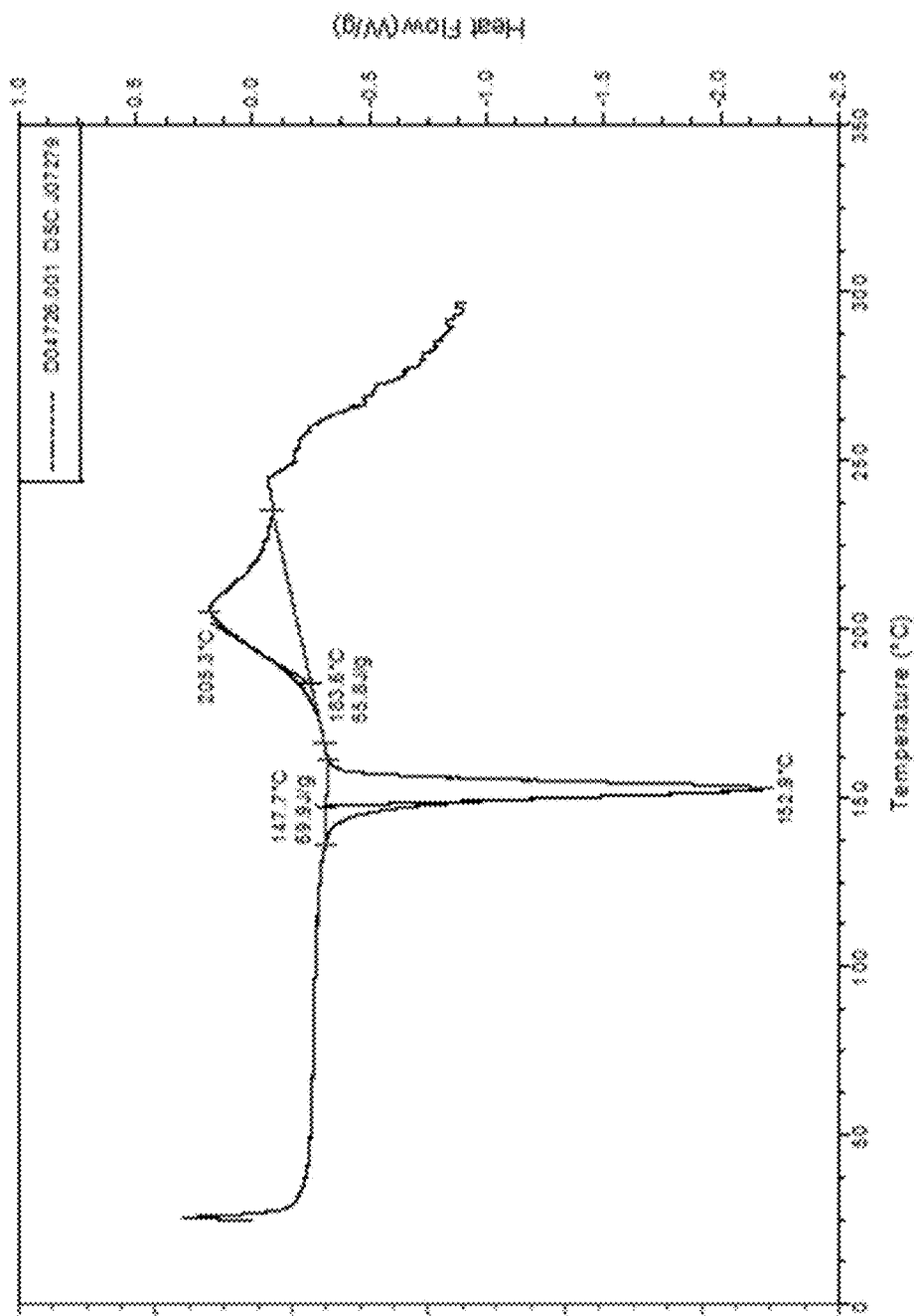
Figure 3:
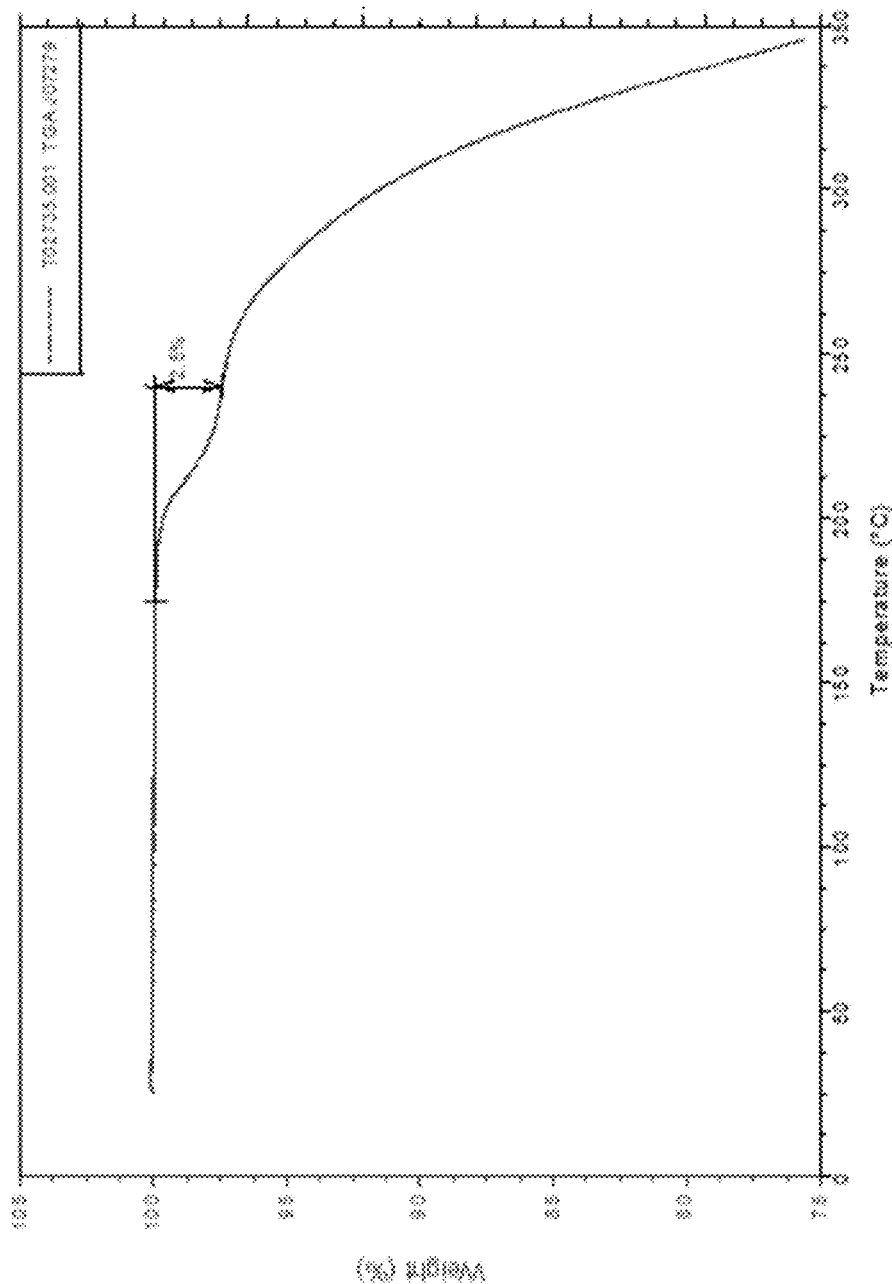
Figure 4:
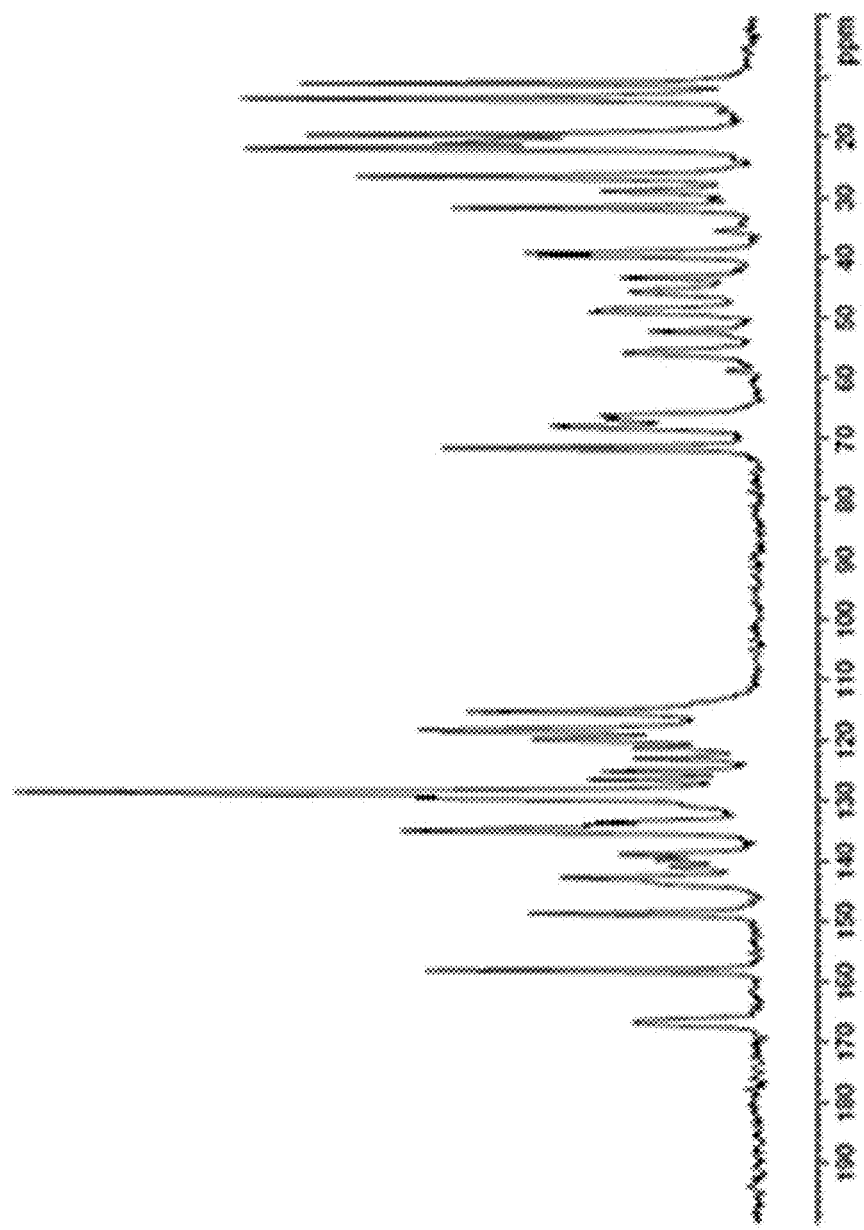
Figure 5:
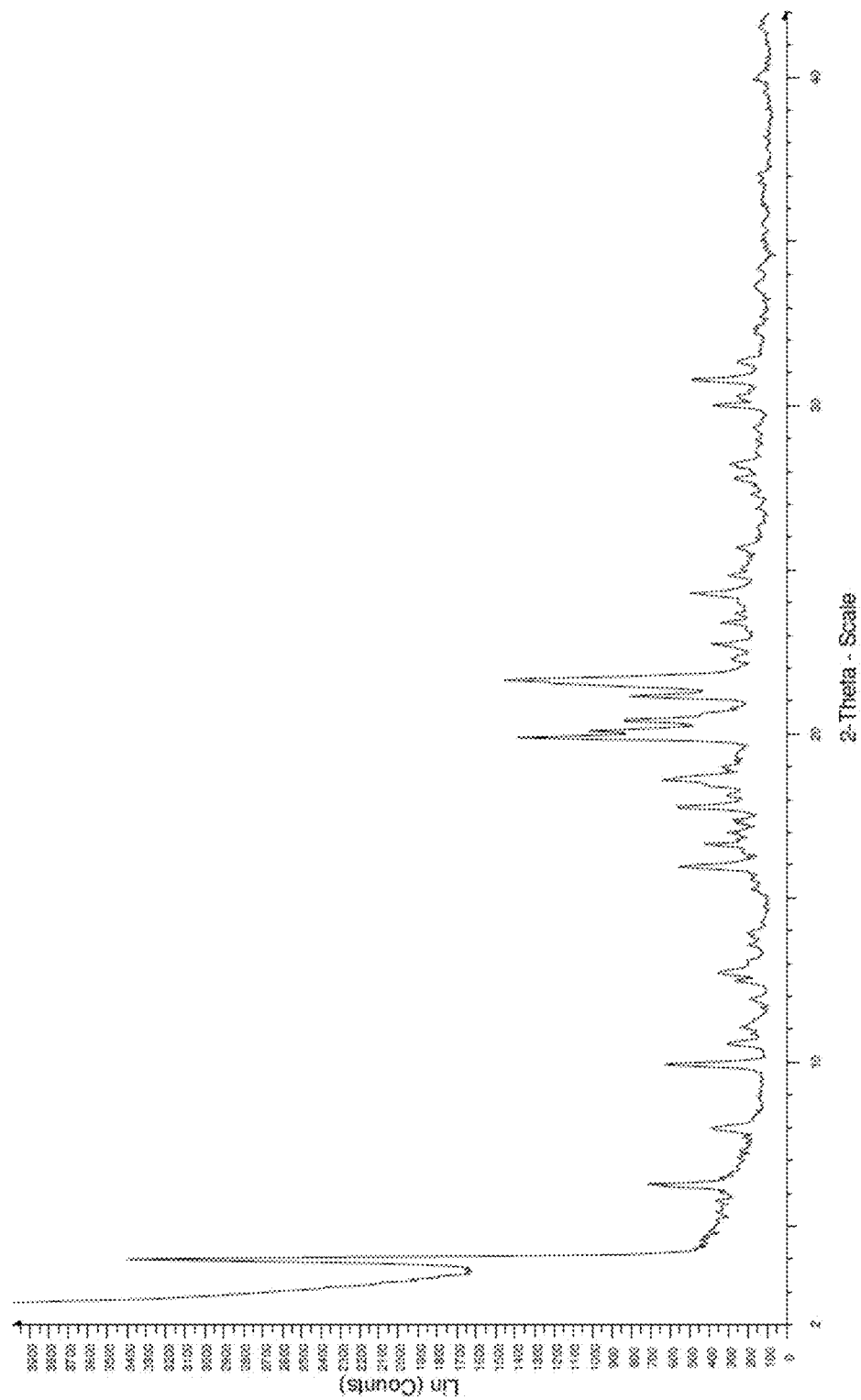
Figure 6:
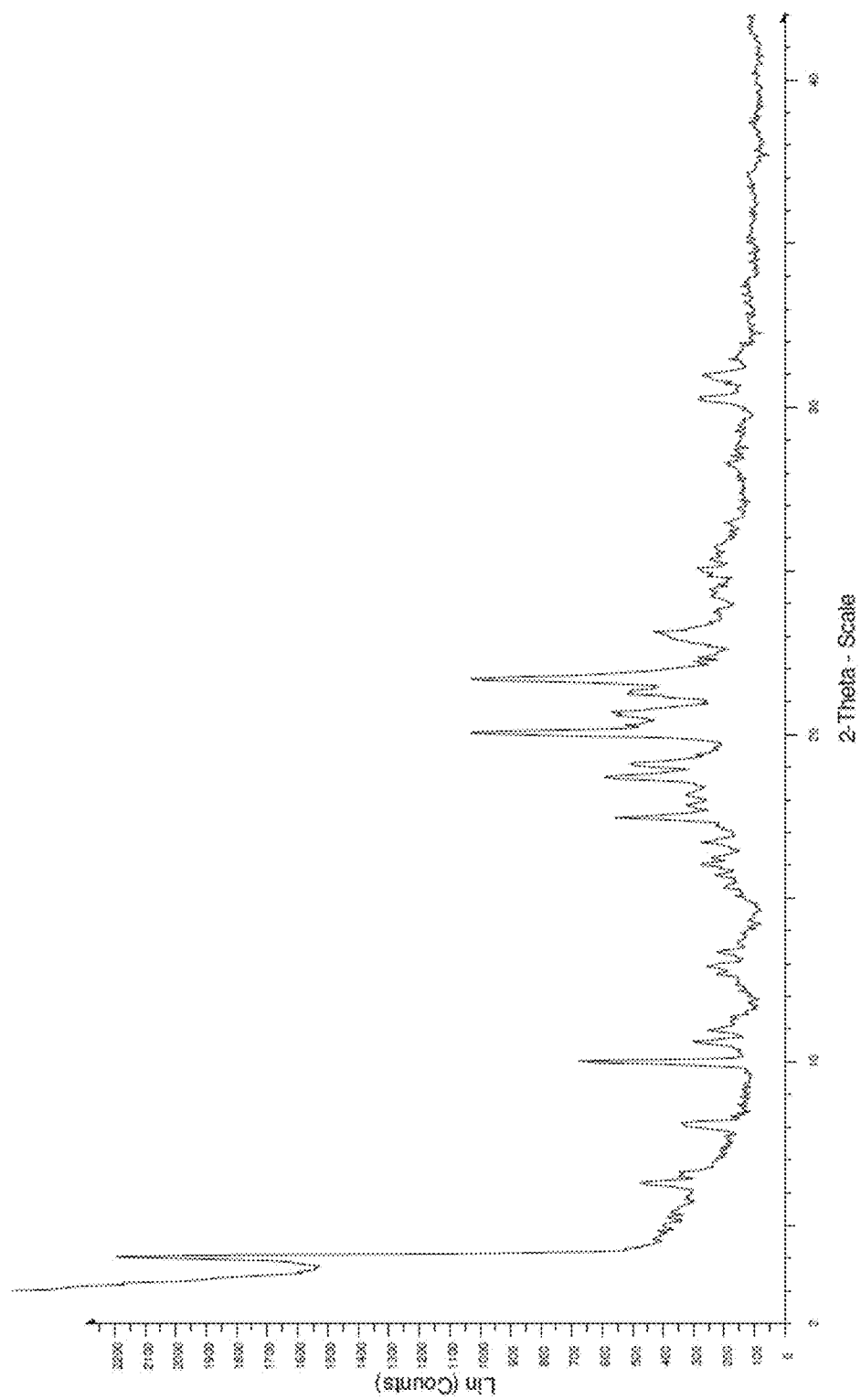
Figure 9:
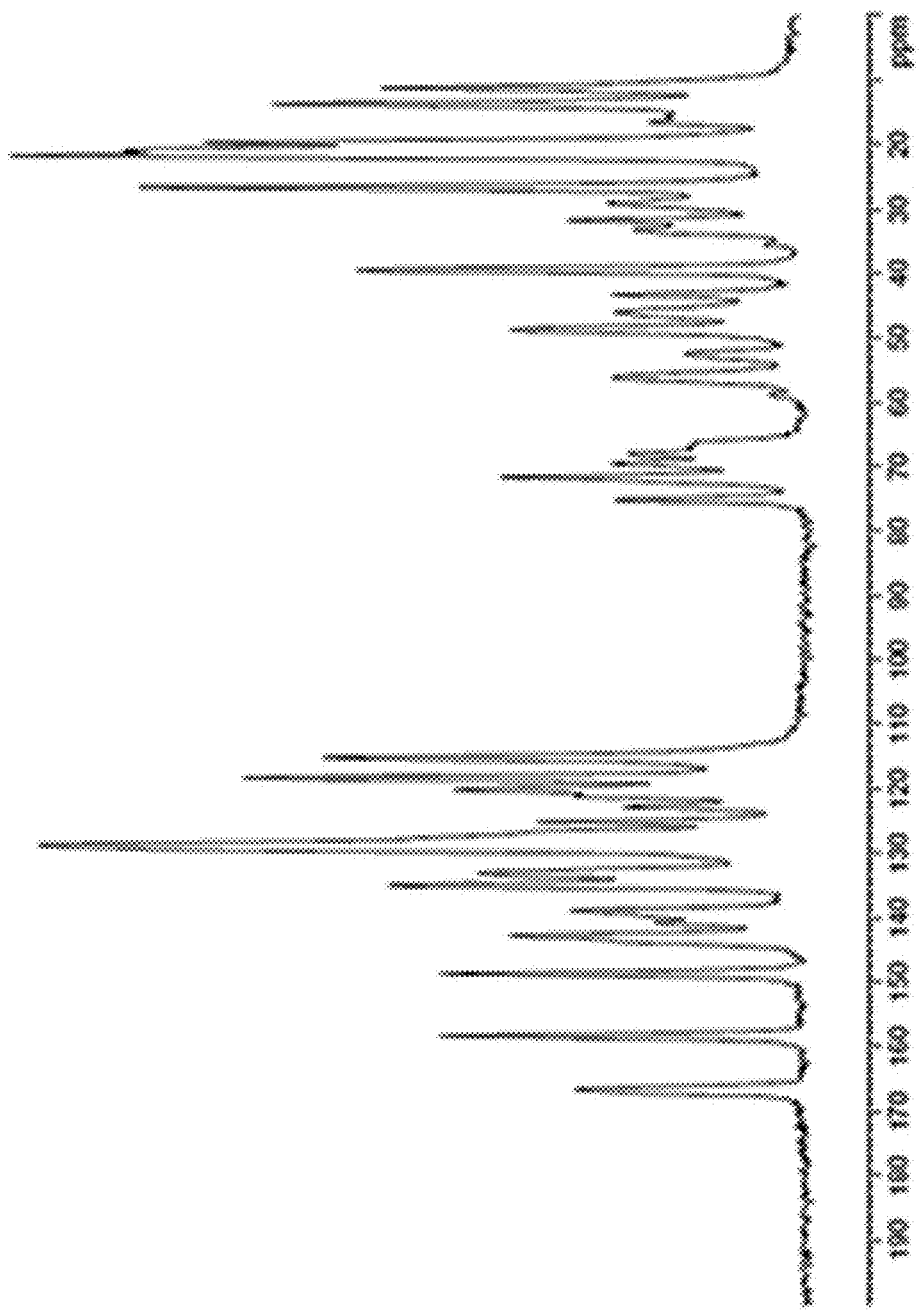
Figure 10:
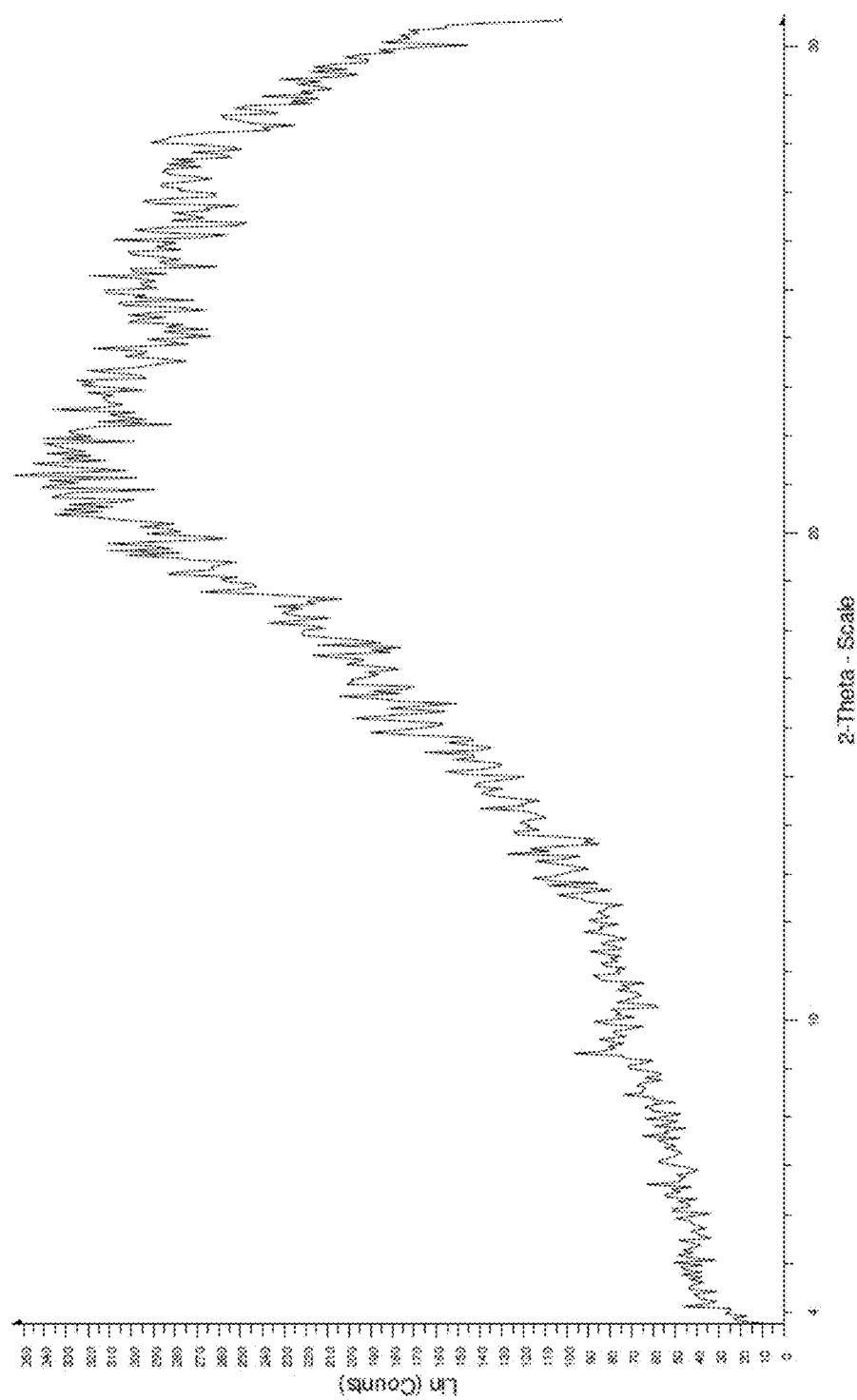
Figure 11:
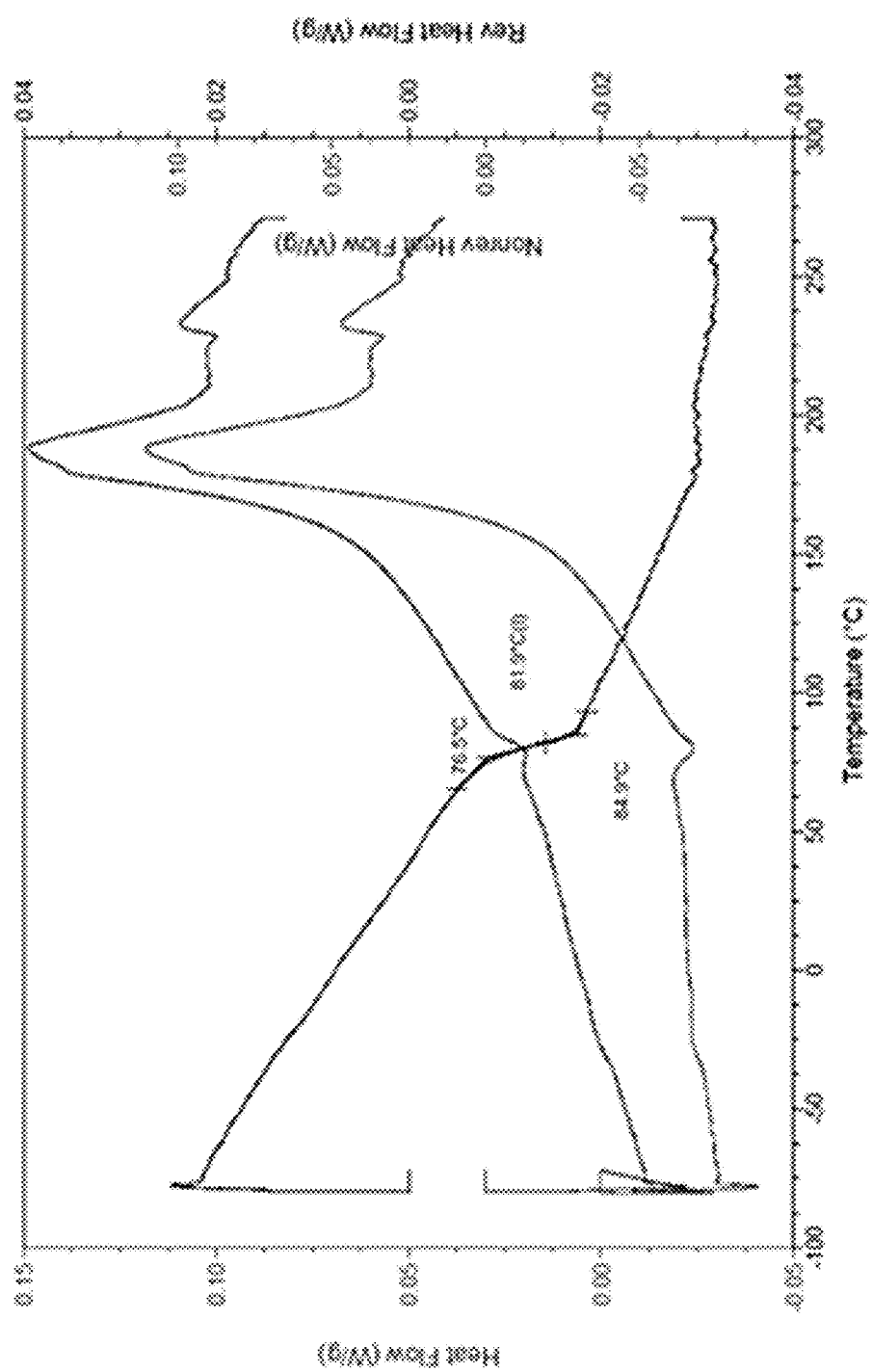
Figure 12B:
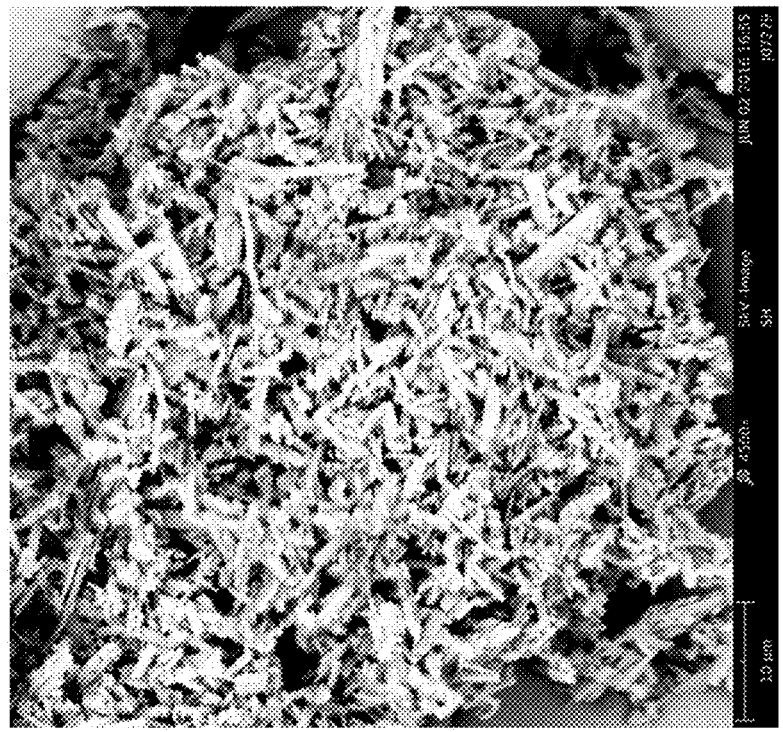
Figure 12A:
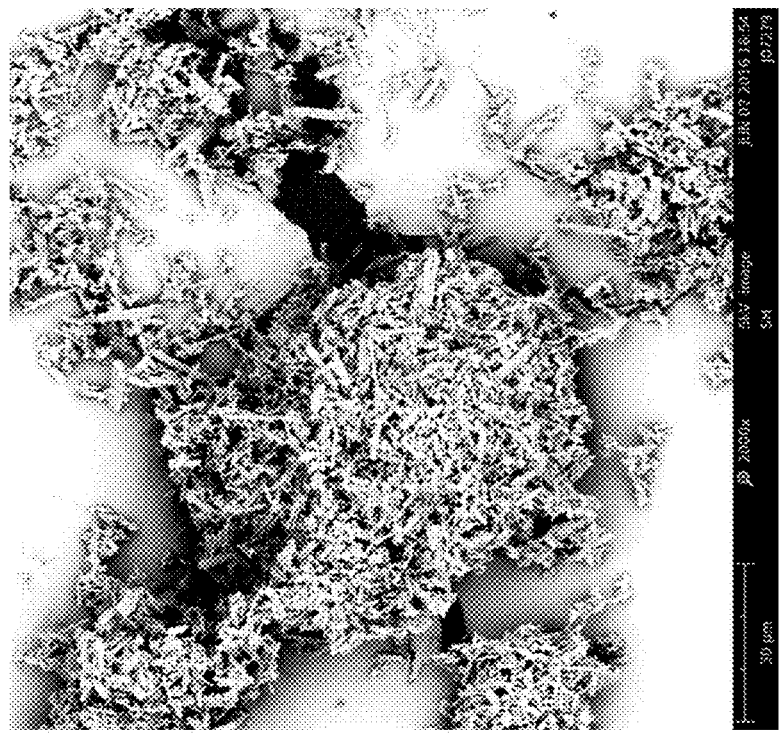
Figure 13B:
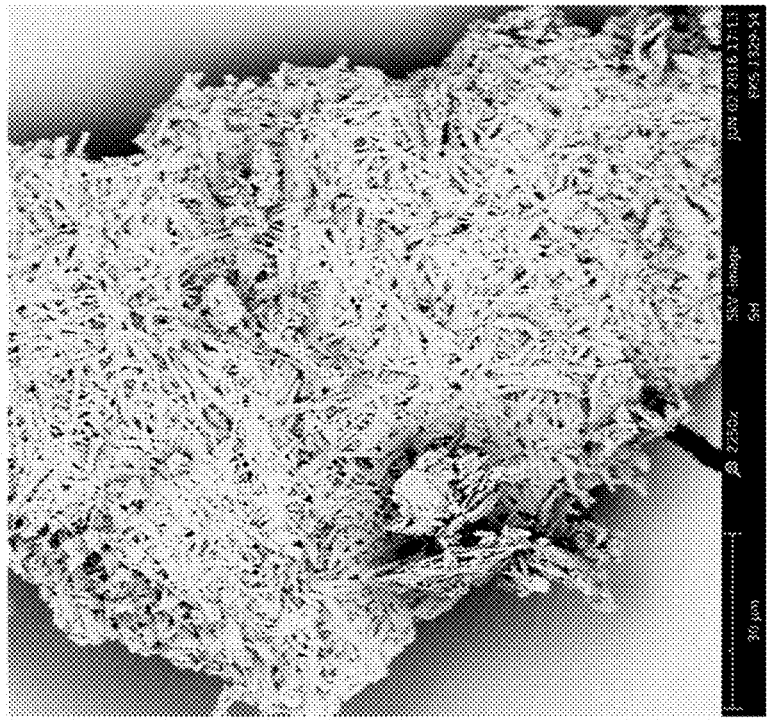
Figure 13A:
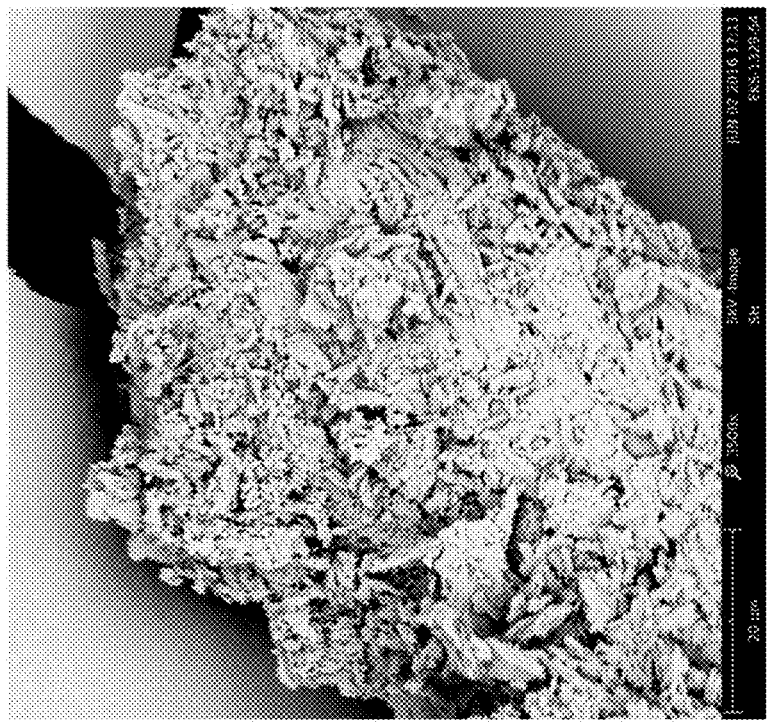

FIG. 1 shows an X-ray powder diffraction (XRPD) pattern of Crystalline Form A of Compound I-MsOH.
FIG. 2 shows a differential scanning calorimetry (DSC) thermogram of Crystalline Form A of Compound I-MsOH.
FIG. 3 shows a thermogravimetric analysis (TGA) thermogram of Crystalline Form A of Compound I-MsOH.
FIG. 4 shows a solid-state $^{13}$C nuclear magnetic resonance (SS $^{13}$C NMR) spectrum of Crystalline Form A of Compound I-MsOH.
FIG. 5 shows an XRPD pattern of Crystalline Form B of Compound I-MsOH.
FIG. 6 shows an XRPD pattern of Crystalline Form C of Compound I-MsOH.
FIG. 7 shows a DSC thermogram of Crystalline Form C of Compound I-MsOH.
FIG. 8 shows a TGA thermogram of Crystalline Form C of Compound I-MsOH.
FIG. 9 shows a SS $^{13}$C NMR spectrum of Crystalline Form C of Compound I-MsOH.
FIG. 10 shows an XRPD pattern of amorphous Compound I-MsOH.
FIG. 11 shows a modulated DSC thermogram of amorphous Compound I-MsOH.
FIGS. 12A and 12B show scanning electron micrograph images of Crystalline Form A of Compound I-MsOH.
FIGS. 13A and 13B show scanning electron micrograph images of Crystalline Form C of Compound I-MsOH.

DETAILED DESCRIPTION OF THE DISCLOSURE

Definitions

While the following terms are believed to be well understood by one of ordinary skill in the art, the following definitions are set forth to facilitate explanation of the presently disclosed subject matter.

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±15% or ±10%, in another example ±5%, in another example ±1%, and in yet another example ±0.1% from the specified amount, as such variations are appropriate to perform the disclosed method.

The term "a" or "an" refers to one or more of that entity; for example, "a halogen" refers to one or more halogens or at least one halogen. As such, the terms "a" (or "an"), "one or more" and "at least one" are used interchangeably herein. In addition, reference to "an alkyl group" by the indefinite article "a" or "an" does not exclude the possibility that more than one of the alkyl group is present (e.g., one or more, or two or more), unless the context clearly requires that there is one and only one of the alkyl groups.

"Administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, and transdermal. "Administering" can also include prescribing or filling a prescription for a dosage form comprising a particular compound. "Administering" can also include providing directions to carry out a method involving a particular compound or a dosage form comprising the compound.

The term "compound(s) of the present invention" or "present compound(s)" refers to the polymorphic and amorphous forms of (S)-8-(4-(2-Butoxyethoxy)phenyl)-1-(2-methylpropyl)-N-(4-(((1-propyl-1H-imidazol-5-yl)methyl)sulfinyl)phenyl)-1,2,3,4-tetrahydrobenzo[b]azocine-5-carboxamide methanesulfonic acid salt (Compound I-MsOH or CVC mesylate)

As used herein, the phrase "aprotic solvent," "nonprotic solvent" or "non-protic solvent" refers to an organic solvent or mixtures of organic solvents that is not readily deprotonated in the presence of a strongly basic reactant. Non-limiting examples of non-protic solvents include ethers, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide, diethoxymeth-

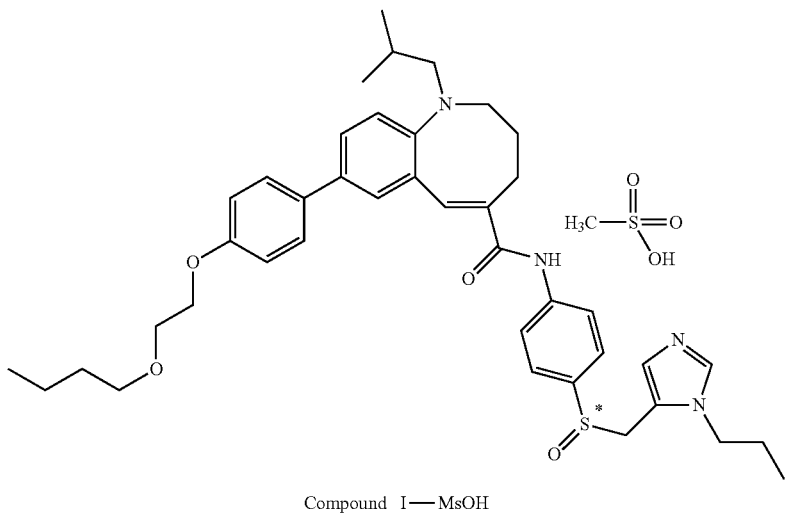

Compound I—MsOH

As used herein, the verb "comprise" as is used in this description and in the claims and its conjugations are used in its non-limiting sense to mean that items following the word are included, but items not specifically mentioned are not excluded.

The term "isomer" refers to compounds having the same chemical formula but may have different stereochemical formula, structural formula, or special arrangements of atoms. Examples of isomers include stereoisomers, diastereomers, enantiomers, conformational isomers, rotamers, geometric isomers, and atropisomers.

"Pharmaceutical formulation" refers to a formulation of a compound of the disclosure and a medium generally accepted in the art for the delivery of the biologically active compound to mammals, e.g., humans. Such a medium includes all pharmaceutically acceptable carriers, diluents or excipients therefor. The pharmaceutical formulations as described herein may be in various dosage forms, such as oral or solid or both dosage forms. In some embodiments, the present pharmaceutical formulations are in tablet or capsule dosage forms.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

ane, tetrahydrofuran, 1,3-dioxane, 1,4-dioxane, furan, diethyl ether, tetrahydropyran, diisopropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, and the like.

As used herein, the phrase "protic solvent" refers to a solvent or solvent mixtures that is capable of functioning as an acid for purposes of protonating any unreacted, strongly basic reaction intermediates. Non-limiting examples of protic solvents include water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and the like.

As used herein, the phrase "part(s)" when used to describe volume of a liquid refers to an approximate estimate of the volume multiplier to a compound, substance, or liquid in which it refers to or which is stated previously. For example, 50 parts water with respect to Compound A means water with approximately 50 times the volume of Compound A is used.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The term "substantially similar" as used herein means an analytical spectrum, such as XRPD patterns, Raman spectroscopy, and etc., which resembles the reference spectrum to a great degree in both the peak locations and their intensity. In one embodiment a "substantially similar" pattern or spectrum is when the peak locations and/or the peak intensity is within about 10% of the reference spectrum. In one embodiment a "substantially similar" pattern or spectrum is when the peak locations and/or the peak intensity is within about 5% of the reference spectrum. In one embodiment a "substantially similar" pattern or spectrum is when the peak locations and/or the peak intensity is within about 2% of the reference spectrum. In one embodiment a "substantially similar" pattern or spectrum is when the peak locations and the peak intensity is within about 2% of the reference spectrum. In another embodiment a "substantially similar" pattern or spectrum is when the peak locations and the peak intensity is within about 1% of the reference spectrum.

"Therapeutically effective amount" means the amount of an active substance that, when administered to a subject for treating a disease, disorder, or other undesirable medical condition, is sufficient to have a beneficial effect with respect to that disease, disorder, or condition. The therapeutically effective amount will vary depending on the chemical identity and formulation form of the active substance, the disease or condition and its severity, and the age, weight, and other relevant characteristics of the patient to be treated. Determining the therapeutically effective amount of a given active substance is within the ordinary skill of the art and typically requires no more than routine experimentation.

"Treating" includes ameliorating, mitigating, and reducing the instances of a disease or condition, or the symptoms of a disease or condition. Because the instances of many diseases or conditions can be reduced before the disease or condition manifests, treating can also include prophylaxis.

As used herein, the symbol "≤" means "not more than" or "equal to or less than"; "<" means "less than"; "≥" means "not less than" or "equal to or more than"; and ">" means "more than". Furthermore, the numerical numbers, when used herein in connection with purity or impurity content, include not only the exact number but also the approximate range around the number. For example, the phrase "purity of 99.0%" denotes a purity of about 99.0%.

Crystalline Materials

In one embodiment, the present invention provides a crystalline form of a salt and/or solvate of Compound I. In one embodiment, the salt is a methanesulfonic acid (MsOH) addition salt.

In one embodiment, the crystalline forms are characterized by the interlattice plane intervals determined by an X-ray powder diffraction pattern (XRPD). The spectrum of XRPD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRPD can be selected according to the peak locations and their relative intensity to conveniently distinguish this crystalline structure from others. The % intensity of the peaks relative to the most intense peak may be represented as I/Io.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θθ of about "8.716±0.3" denotes a range from about 8.716+0.3, i.e., about 9.016, to about 8.716-0.3, i.e., about 8.416. Depending on the sample preparation techniques, the calibration techniques applied to the instruments, human operational variation, and etc., those skilled in the art recognize that the appropriate error of margins for a XRPD can be about ±0.7; ±0.6; ±0.5; ±0.4; ±0.3; ±0.2; ±0.1; ±0.05; or less.

Additional details of the methods and equipment used for the XRPD analysis are described in the Examples section.

In one embodiment, the crystalline forms are characterized by Differential Scanning calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. A peak characteristic value of a DSC thermogram is often used as the characteristic peak to distinguish this crystalline structure from others.

Those skilled in the art recognize that the measurements of the DSC thermogram for a given crystalline form of the same compound will vary within a margin of error. The values of a single peak characteristic value, expressed in degree C., allow appropriate error margins. Typically, the error margins are represented by "±". For example, the single peak characteristic value of about "53.09±2.0" denotes a range from about 53.09+2, i.e., about 55.09, to about 53.09-2, i.e., about 51.09. Depending on the sample preparation techniques, the calibration techniques applied to the instruments, human operational variations, and etc., those skilled in the art recognize that the appropriate error of margins for a single peak characteristic value can be ±2.5; ±2.0; ±1.5; ±1.0; ±0.5; or less.

Additional details of the methods and equipment used for the DSC and TGA thermogram analysis are described in the Examples section.

In one embodiment, the crystalline form of Compound I is a methanesulfonic acid salt (Compound I-MsOH). In some embodiments, crystalline form of Compound I-MsOH exhibits different polymorphs. Examples of the crystalline form of Compound I-MsOH include, but are not limited to, Crystalline Forms A, B and C, as defined in the following sections.

In one embodiment of the present disclosure, the crystalline form of Compound I-MsOH may comprise of a mixture of one or more forms of polymorphs of Compound I-MsOH. In some embodiments, the crystalline form of Compound I-MsOH may comprise of substantially pure form of one polymorph type. In one embodiment, the crystalline form of Compound I-MsOH may comprise of over about 99.9%, about 99.8%, about 99.7%, about 99.6%, about 99.5%, about 99.4%, about 99.3%, about 99.2%, about 99.1%, or about 99.0% of one polymorph of Compound I-MsOH. In another embodiment, the crystalline form of Compound I-MsOH may comprise over about 99%, about 98%, about 97%, about 96%, about 95%, about 94%, about 93%, about 92%, about 91%, or about 90% of one polymorph of Compound I-MsOH. In some embodiments, the crystalline form of Compound I-MsOH may comprise over about 90%, about 85%, about 80%, about 75%, about 70%, about 65%, about 60%, about 55%, about 50%, about 45%, or about 40% of one polymorph of Compound I-MsOH.

In one embodiment of the present disclosure, the crystalline form of Compound I-MsOH may comprise of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50% of Crystalline Form A of Compound I-MsOH.

In one embodiment of the present disclosure, the crystalline form of Compound I may be Crystalline Form A of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, 1 about 8%, about 19%, about 20%, about 25%, about 30%, about 35%, about 40%, about 45% or about 50% of Crystalline Forms B or C, or mixtures thereof.

In one embodiment of the present disclosure, the crystalline form of Compound I-MsOH may be Crystalline Form A of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50% of Crystalline Form B.

In one embodiment of the present disclosure, the crystalline form of Compound I-MsOH may be Crystalline Form A of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50% of Crystalline Form C.

In one embodiment of the present disclosure, the crystalline form of Compound I-MsOH may comprise of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50% of Crystalline Form B of Compound I-MsOH.

In one embodiment of the present disclosure, the crystalline form of Compound I may be Crystalline Form B of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50% of Crystalline Forms A or C, or mixtures thereof.

In one embodiment of the present disclosure, the crystalline form of Compound I-MsOH may be Crystalline Form B of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50% of Crystalline Form A.

In one embodiment of the present disclosure, the crystalline form of Compound I-MsOH may be Crystalline Form B of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, 3 about 0%, about 35%, about 40%, about 45% or about 50% of Crystalline Form C.

In one embodiment of the present disclosure, the crystalline form of Compound I-MsOH may comprise of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50% of Crystalline Form C of Compound I-MsOH.

In one embodiment of the present disclosure, the crystalline form of Compound I may be Crystalline Form C of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50% of Crystalline Forms A or B, or mixtures thereof.

In one embodiment of the present disclosure, the crystalline form of Compound I-MsOH may be Crystalline Form C of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50% of Crystalline Form A.

In one embodiment of the present disclosure, the crystalline form of Compound I-MsOH may be Crystalline Form C of Compound I-MsOH comprising about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50% of Crystalline Form B.

Crystalline Form A

In one embodiment, Crystalline Form A of Compound I-MsOH (Crystalline Form A) exhibits an XRPD comprising one or more peaks at about 4.0, about 18.7, about 19.1, about 20.1 and about 21.7 degrees two-theta with the margin of error of about ±0.5; about ±0.4; about ±0.3; about ±0.2; about ±0.1; about ±0.05; or less. In another embodiment, the XRPD of the Crystalline Form A further comprises one or more peaks at about 10.0, about 17.4, about 20.4, about 20.7, and about 23.2 degrees two-theta with the margin of error of about ±0.5; about ±0.4; about ±0.3; about ±0.2; about ±0.1; about ±0.05; or less. In further embodiment, the Crystalline Form A further comprises one or more peaks at about 6.3, about 20.8, about 21.3, about 22.0 and about 23.8 degrees two-theta with the margin of error of about ±0.5; about ±0.4; about ±0.3; about ±0.2; about ±0.1; about ±0.05; or less. In another embodiment, the Crystalline Form A further comprises one or more peaks at about 8.1, about 13.4, about 18.1, about 22.2 and about 22.8 degrees two-theta with the margin of error of about ±0.5; about ±0.4; about ±0.3; about ±0.2; about ±0.1; about ±0.05; or less. In yet another embodiment, the Crystalline Form A exhibits an XRPD comprising peaks shown in Table 1. In one embodiment, the Crystalline Form A exhibits an XRPD comprising peaks substantially similar to peaks shown in Table 1.

TABLE 1

XRPD Table of Crystalline Form A

| 2-Theta | Intensity % |
|---|---|
| 4.0 | 100.0 |
| 5.5 | 10.0 |
| 6.3 | 22.4 |
| 6.6 | 11.8 |
| 8.1 | 18.4 |
| 10.0 | 38.4 |
| 10.2 | 8.2 |
| 10.6 | 15.3 |
| 10.9 | 10.6 |
| 12.2 | 9.4 |
| 12.4 | 14.1 |
| 12.7 | 12.2 |
| 12.9 | 16.9 |

TABLE 1-continued

XRPD Table of Crystalline Form A

| 2-Theta | Intensity % |
|---|---|
| 13.4 | 18.8 |
| 13.6 | 9.0 |
| 15.0 | 13.7 |
| 15.4 | 13.7 |
| 15.7 | 16.1 |
| 16.3 | 11.4 |
| 16.8 | 10.6 |
| 17.4 | 48.6 |
| 18.1 | 18.8 |
| 18.7 | 65.1 |
| 19.1 | 52.9 |
| 19.5 | 9.8 |
| 20.1 | 62.0 |
| 20.4 | 39.6 |
| 20.7 | 35.7 |
| 20.8 | 22.7 |
| 21.3 | 31.8 |
| 21.7 | 67.5 |
| 22.0 | 19.6 |
| 22.2 | 18.8 |
| 22.8 | 18.8 |
| 23.2 | 48.2 |
| 23.5 | 11.0 |
| 23.8 | 21.6 |
| 24.2 | 14.5 |
| 24.6 | 13.3 |
| 24.9 | 12.2 |
| 25.1 | 14.9 |
| 25.4 | 14.1 |
| 25.8 | 10.2 |
| 26.2 | 14.5 |
| 26.5 | 12.2 |

In one specific embodiment, the Crystalline Form A exhibits an XRPD that is substantially similar to FIG. 1.

In one embodiment, the Crystalline Form A exhibits a DSC thermogram comprising a sharp endotherm at about 152.9° C. with the error of margin of about ±2.5; about ±2.0; about ±1.5; about ±1.0; about ±0.5; or less. In one specific embodiment, the Crystalline Form A exhibits a DSC thermogram that is substantially similar to FIG. 2.

In one embodiment, the Crystalline Form A exhibits a TGA thermogram that is substantially similar to FIG. 3. In other embodiments, the TGA thermogram of the Crystalline Form A exhibits a weight loss of 0.0 to about 2.5% in the temperature range of 25 to 250° C.

In one embodiment, the Crystalline Form A exhibits a solid-state $^{13}$C NMR spectrum that is substantially similar to FIG. 4.

Crystalline Form B

In one embodiment, Crystalline Form B of Compound I-MsOH (Crystalline Form B) exhibits an XRPD comprising one or more peaks at about 4.0, about 15.9, about 17.8, about 19.9, about 20.1, about 21.5 and about 21.6 degrees two-theta with the margin of error of about ±0.5; about ±0.4; about ±0.3; about ±0.2; about ±0.1; about ±0.05; or less. In another embodiment, the XRPD of the Crystalline Form B further comprises one or more peaks at about 6.3, about 9.9, about 18.6, about 20.4 and about 21.1 degrees two-theta with the margin of error of about ±0.5; about ±0.4; about ±0.3; about ±0.2; about ±0.1; about ±0.05; or less. In further embodiment, the Crystalline Form B further comprises one or more peaks at about 15.9, about 16.6, about 17.8, about 18.4 and about 24.3 degrees two-theta with the margin of error of about ±0.5; about ±0.4; about ±0.3; about ±0.2; about ±0.1; about ±0.05; or less. In another embodiment, the Crystalline Form B further comprises one or more peaks at about 5.7, about 6.5, about 7.9, about 12.7 and about 22.7 degrees two-theta with the margin of error of about ±0.5; about ±0.4; about ±0.3; about ±0.2; about ±0.1; about ±0.05; or less. In yet another embodiment, the Crystalline Form B exhibits an XRPD comprising peaks shown in Table 2. In one embodiment, the Crystalline Form B exhibits an XRPD comprising peaks substantially similar to peaks shown in Table 2.

TABLE 2

XRPD Table of Crystalline Form B

| 2-Theta | Intensity % |
|---|---|
| 4.0 | 100.0 |
| 5.7 | 10.8 |
| 6.0 | 9.8 |
| 6.3 | 21.1 |
| 6.5 | 10.6 |
| 6.6 | 8.7 |
| 7.7 | 6.6 |
| 7.9 | 11.3 |
| 8.3 | 5.5 |
| 9.9 | 18.5 |
| 10.6 | 9.2 |
| 10.8 | 5.5 |
| 11.0 | 7.2 |
| 11.9 | 5.7 |
| 12.4 | 7.9 |
| 12.7 | 10.6 |
| 13.0 | 5.8 |
| 13.1 | 5.8 |
| 13.5 | 6.0 |
| 13.8 | 5.7 |
| 13.9 | 6.2 |
| 15.2 | 5.5 |
| 15.5 | 5.7 |
| 15.7 | 5.5 |
| 15.9 | 16.4 |
| 16.3 | 5.8 |
| 16.6 | 12.8 |
| 16.8 | 7.5 |
| 17.0 | 9.2 |
| 17.3 | 7.9 |
| 17.4 | 8.1 |
| 17.8 | 16.8 |
| 18.1 | 9.4 |
| 18.4 | 12.5 |
| 18.6 | 18.7 |
| 18.9 | 9.1 |
| 19.0 | 10.0 |
| 19.2 | 7.9 |
| 19.3 | 7.9 |
| 19.4 | 7.9 |
| 19.9 | 41.3 |
| 20.1 | 30.0 |
| 20.4 | 24.7 |
| 20.8 | 8.5 |
| 21.1 | 23.6 |
| 21.5 | 36.0 |
| 21.6 | 43.2 |
| 22.3 | 8.7 |
| 22.4 | 7.4 |
| 22.6 | 7.7 |
| 22.7 | 11.5 |
| 23.4 | 10.0 |
| 23.7 | 7.7 |
| 24.0 | 7.7 |
| 24.3 | 14.3 |
| 24.8 | 8.9 |
| 25.1 | 6.8 |
| 25.4 | 6.0 |
| 25.7 | 7.7 |
| 26.0 | 4.9 |

In one specific embodiment, the Crystalline Form B exhibits an XRPD that is substantially similar to FIG. 5.

Crystalline Form C

In one embodiment, Crystalline Form C of Compound I-MsOH (Crystalline Form C) exhibits an XRPD comprising one or more peaks at about 4.0, about 10.0, about 16.0, about 18.7, about 20.0 and about 21.7 degrees two-theta with the margin of error of about ±0.5; about ±0.4; about ±0.3; about ±0.2; about ±0.1; about ±0.05; or less. In another embodiment, the XRPD of the Crystalline Form C further comprises one or more peaks at about 17.4, about 20.3, about 20.6, about 20.7 and about 21.2 degrees two-theta with the margin of error of about ±0.5; about ±0.4; about ±0.3; about ±0.2; about ±0.1; about ±0.05; or less. In further embodiment, the Crystalline Form C further comprises one or more peaks at about 6.3, about 6.5, about 19.1, about 21.3 and about 23.1 degrees two-theta with the margin of error of about ±0.5; about ±0.4; about ±0.3; about ±0.2; about ±0.1; about ±0.05; or less. In another embodiment, the Crystalline Form C further comprises one or more peaks at about 6.6, about 8.1, about 17.8, about 18.1 and about 23.3 degrees two-theta with the margin of error of about ±0.5; about ±0.4; about ±0.3; about ±0.2; about ±0.1; about ±0.05; or less. In yet another embodiment, the Crystalline Form C exhibits an XRPD comprising peaks shown in Table 3. In one embodiment, the Crystalline Form C exhibits an XRPD comprising peaks substantially similar to peaks shown in Table 3.

TABLE 3

XRPD Table of Crystalline Form C

| 2-Theta | Intensity % |
|---|---|
| 4.0 | 100.0 |
| 6.3 | 21.7 |
| 6.5 | 15.9 |
| 6.6 | 15.6 |
| 8.1 | 15.6 |
| 10.0 | 31.0 |
| 10.6 | 13.9 |
| 10.9 | 11.5 |
| 11.2 | 8.3 |
| 11.3 | 8.3 |
| 11.8 | 5.6 |
| 12.1 | 6.9 |
| 12.3 | 7.4 |
| 12.7 | 10.5 |
| 12.9 | 11.7 |
| 13.4 | 10.5 |
| 13.6 | 7.2 |
| 13.9 | 6.9 |
| 14.0 | 6.3 |
| 14.3 | 5.8 |
| 14.5 | 5.0 |
| 15.0 | 7.8 |
| 15.3 | 9.0 |
| 15.7 | 10.5 |
| 16.0 | 12.7 |
| 16.3 | 11.2 |
| 16.7 | 12.5 |
| 16.8 | 10.4 |
| 17.1 | 9.7 |
| 17.2 | 10.4 |
| 17.4 | 25.6 |
| 17.8 | 14.9 |
| 18.1 | 14.9 |
| 18.7 | 27.1 |
| 19.1 | 23.4 |
| 19.4 | 13.4 |
| 19.6 | 11.0 |
| 20.0 | 46.8 |
| 20.3 | 23.8 |
| 20.6 | 24.9 |
| 20.7 | 26.2 |
| 21.2 | 23.8 |
| 21.3 | 23.4 |
| 21.7 | 46.8 |
| 22.2 | 13.6 |

TABLE 3-continued

XRPD Table of Crystalline Form C

| 2-Theta | Intensity % |
|---|---|
| 22.3 | 12.8 |
| 23.1 | 19.5 |
| 23.3 | 14.9 |
| 23.5 | 11.5 |
| 23.7 | 11.0 |
| 24.2 | 11.2 |
| 24.5 | 11.2 |
| 24.8 | 11.3 |
| 25.0 | 12.6 |
| 25.1 | 13.0 |
| 25.4 | 11.3 |
| 25.5 | 10.2 |
| 25.7 | 10.4 |
| 26.1 | 8.7 |
| 26.2 | 8.4 |
| 26.5 | 9.3 |

In one specific embodiment, the Crystalline Form C exhibits an XRPD that is substantially similar to FIG. 6.

In one embodiment, the Crystalline Form C exhibits a DSC thermogram comprising a sharp endotherm at about 151.5° C. with the error of margin of about ±2.5; about ±2.0; about ±1.5; about ±1.0; about ±0.5; or less. In another embodiment, the Crystalline Form C further exhibits a DSC thermogram comprising one or more of the following peaks: endotherm at about 126.7±2.0° C. and exotherm at about 205.2±2.0° C. In one specific embodiment, the Crystalline Form C exhibits a DSC thermogram that is substantially similar to FIG. 7.

In one embodiment, the Crystalline Form C exhibits a TGA thermogram that is substantially similar to FIG. 8. In another embodiment, the TGA thermogram of the Crystalline Form C exhibits a 0.0 to about 2.5% weight loss in the temperature range of 25 to 250° C.

Methods of Isolating Crystalline Materials

In certain embodiments, the crystalline polymorphs of Compound I-MsOH are isolated after they are prepared. The isolation of the crystalline polymorphs may be accomplished using methods such as filtration, decantation, or other suitable separation technique.

In certain embodiments, the isolated crystalline polymorphs are optionally washed with a liquid such as an anti-solvent, acetonitrile, methanol, ethanol, ethyl acetate, methyl ethyl ketone, acetone, tetrahydrofuran, or a combination thereof. In particular embodiments, the isolated crystalline polymorphs are washed with a combination of anti-solvent and an organic solvent.

Crystalline Form A

In certain embodiments, methods of making Crystalline Form A of Compound I-MsOH (Crystalline Form A) are provided.

In one embodiment, the method of making Crystalline Form A comprises (a) suspending a Compound I-MsOH in a suitable solvent to form a slurry and (b) isolating Crystalline Form A. In further embodiments, the suspending step (a) is conducted at about 5° C., or about 50° C. In further embodiments, the suspending step (a) is conducted overnight. In further embodiments, the suspending step (a) is conducted for about 12 hours. In an embodiment carried out at about 5° C. the solvent is selected from ethyl acetate, isopropyl acetate, methyl isobutyl ketone, isopropanol, ethanol, 2-methyl-1-propanol, propyl acetate, acetonitrile, 1,2-dimethoxyethane, nitromethane, ethyl acetate/acetonitrile (e.g., 50/50); ethyl acetate/acetonitrile/water (e.g., 47.5/47.5/5); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) and acetonitrile/dichloromethane (e.g., 95/5). In an embodiment carried out at about 50° C. the solvent is selected from ethyl acetate, isopropyl acetate, methyl isobutyl ketone, isopropanol, methyl ethyl ketone, acetone, tert-butyl methyl ether, anisole, toluene, acetonitrile, 1,2-dimethoxyethane, ethyl acetate/acetonitrile (e.g., 50/50); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) and acetonitrile/dichloromethane (e.g., 95/5). In still further embodiments, the Compound I-MsOH used in step (a) is amorphous.

In another embodiment, the method of making Crystalline Form A comprises (a) suspending a Compound I-MsOH in a suitable solvent to form a slurry, (b) maturating the slurry at about 25° C. and then about 50° C., (c) isolating Crystalline Form A, and (d) drying the isolated product under vacuum, and breaking up product to dry at above 30° C. In one embodiment, the isolating step (b) is conducted by filtration. In further embodiments, the drying at above 30° C. is conducted at a temperature that converts substantially all of the Crystalline Form B and/or Crystalline Form C present in the product into Crystalline Form A. More particularly, the drying is done at about 40° C. In further embodiments, the maturating step (a) is conducted at about four hours for each of the temperatures. In an embodiment carried out at about 5° C. the solvent is selected from ethyl acetate, isopropyl acetate, methyl isobutyl ketone, isopropanol, methyl ethyl ketone, acetone, 2-methyl-1-propanol, tert-butyl methyl ether, anisole, toluene, tetrahydrofuran, acetonitrile, 1,2-dimethoxyethane, nitromethane, ethyl acetate/acetonitrile (e.g., 50/50); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) and acetonitrile/dichloromethane (e.g., 95/5). In still further embodiments, the Compound I-MsOH used in step (a) is amorphous.

In one embodiment, the method of making Crystalline Form A comprises (a) suspending a Compound I-MsOH in a suitable solvent at a temperature of about 5° C., (b) heating the suspension of step (a) at about 50° C., (c) isolating Crystalline Form A, and (d) drying the isolated product under vacuum, and breaking up the product and drying at above 30° C. In some embodiments, the suspension formed in step (a) is a slurry. In one embodiment, the heating step (b) is maturating the suspension of step (a). In one embodiment, the isolating step (b) is conducted by filtration. In one embodiment, the drying step (d) is at about 40° C. In an embodiment, the solvent is selected from ethyl acetate, isopropyl acetate, methyl isobutyl ketone, isopropanol, methyl ethyl ketone, acetone, 2-methyl-1-propanol, tert-butyl methyl ether, anisole, toluene, tetrahydrofuran, acetonitrile, 1,2-dimethoxyethane, nitromethane, ethyl acetate/acetonitrile (e.g., 50/50); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) or acetonitrile/dichloromethane (e.g., 95/5). In still further embodiments, the Compound I-MsOH used in step (a) is amorphous.

In one embodiment, the method of making Crystalline Form A comprises (a) suspending a Compound I-MsOH in a suitable solvent at a temperature of about 25° C., (b) heating the suspension of step (a) at about 50° C., (c) isolating Crystalline Form A, and (d) drying the isolated product under vacuum, and breaking up the product and drying at above 30° C. In some embodiments, the suspension formed in step (a) is a slurry. In one embodiment, the heating step (b) is maturing the suspension of step (a). In one embodiment, the isolating step (b) is conducted by filtration. In one embodiment, the drying step (d) is at about 40° C. In an embodiment, the solvent is selected from ethyl acetate, isopropyl acetate, methyl isobutyl ketone, isopropanol, methyl ethyl ketone, acetone, 2-methyl-1-propanol, tert-butyl methyl ether, anisole, toluene, tetrahydrofuran, acetonitrile, 1,2-dimethoxyethane, nitromethane, ethyl acetate/acetonitrile (e.g., 50/50); ethyl acetate/acetonitrile/pyridine (e.g., 47.5/47.5/5); ethyl acetate/acetonitrile/dichloromethane (e.g., 47.5/47.5/5); acetonitrile/ethyl acetate (e.g., 95/5); acetonitrile/pyridine (e.g., 95/5) or acetonitrile/dichloromethane (e.g., 95/5). In still further embodiments, the Compound I-MsOH used in step (a) is amorphous.

In another embodiment, the method of making Crystalline Form A comprises (a) adding to a solution of Compound I-MsOH in a suitable solvent an anti-solvent to precipitate Crystalline Form A, and (b) isolating Crystalline Form A. In yet another embodiment, the method of making Crystalline Form A comprises (a) adding to a solution of Compound I-MsOH in a suitable solvent an anti-solvent to form an oil that converts to Crystalline Form A, and (b) isolating Crystalline Form A. In further embodiments, the solution of step (a) is at about 25° C. In further embodiments, the conversion of the oil of step (a) is at about 25° C. In an embodiment where Crystalline Form A precipitates, the solvent/anti-solvent combination is methanol/tert-butyl methyl ether. In an embodiment where an oil is formed that converts to Crystalline Form A, the solvent/anti-solvent combination is selected from ethanol:water (e.g., 90:10)/tert-butyl methyl ether, ethyl acetate:acetonitrile:water (e.g., 47.5:47.5:5)/tert-butyl methyl ether, and methanol/tert-butyl methyl ether. In still further embodiments, the Compound I-MsOH used in step (a) is amorphous.

In another embodiment, the method of making Crystalline Form A comprises (a) evaporating a solution of Compound I-MsOH at ambient conditions to precipitate Crystalline Form A, and (b) isolating Crystalline Form A. In one embodiment, the method of making Crystalline Form A comprises (a) dissolving a Compound I-MsOH in a suitable solvent, (b) evaporating a portion of the suitable solvent from the solution of step (a), and (c) isolating Crystalline Form A. In an embodiment where Crystalline Form A precipitates after evaporation of the solvent, wherein the solvent is selected from anisole, 2-methyl-1-propanol and isopropanol:water (e.g., 90:10). In further embodiments, the Compound I-MsOH used in step (a) is amorphous.

In yet another embodiment, the method of making Crystalline Form A comprises (a) suspending a Compound I-MsOH in a suitable solvent; (b) milling the suspension of step (a); and (c) isolating Crystalline Form A of Compound I-MsOH. In further embodiments, the Compound I-MsOH used in step (a) is amorphous. In still further embodiments, the milling step (b) is conducted using a ball mill. In further embodiments, the milling step (b) is conducted for about two hours. In an embodiment, the solvent is selected from isopropanol, acetone, ethanol, acetonitrile, and nitromethane. In further embodiments, the Compound I-MsOH used in step (a) is amorphous.

In one embodiment, the method of making Crystalline Form A of Compound I-MsOH comprises (a) preparing amorphous Compound I-MsOH, (b) dissolving or suspending the amorphous Compound I-MsOH in a suitable solvent, (c) inducing the formation of Crystalline Form B, (d) inducing the Crystalline Form B to convert to Crystalline Form C, and (e) inducing the Crystalline Form C to convert to Crystalline Form A. In further embodiments, the Crystalline Form C is converted to Crystalline Form A by drying the Crystalline Form C at a temperature of about 40° C. In a preferred embodiment, substantially all of the Crystalline Form C is converted into Crystalline Form A by drying the Crystalline Form C at a temperature above 30° C.

In other embodiments, the Crystalline Form A prepared by the embodiments above is substantially pure. For example, polymorphic purity of the Crystalline Form A may comprise at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50% of Crystalline Form A of Compound I-MsOH.

Crystalline Form B

In certain embodiments, methods of making Crystalline Form B of Compound I-MsOH (Crystalline Form B) are provided.

In one embodiment, the method of making Crystalline Form B comprises (a) suspending Compound I-MsOH in a suitable solvent and (b) forming a suspension of Crystalline Form B of Compound I-MsOH in the solvent. In an embodiment, the suspension forms at about 5° C. where the solvent is selected from methyl ethyl ketone, acetone and tetrahydrofuran. In an embodiment, the suspension forms at about 25° C. where the solvent is selected from acetone and tetrahydrofuran. In further embodiments, the Compound I-MsOH used in step (a) is amorphous.

In yet another embodiment, the method of making Crystalline Form B comprises (a) dissolving a Compound I-MsOH in a suitable solvent; (b) adding a suitable anti-solvent to the solution of step (a); and (c) forming a suspension of Crystalline Form B of Compound I-MsOH. In an embodiment, the suspension forms at about 5° C. or about 25° C. where the suitable solvent is dichloromethane and the suitable anti-solvent is n-heptane. In further embodiments, the Compound I-MsOH used in step (a) is amorphous.

In other embodiments, the Crystalline Form B prepared by the embodiments above is substantially pure. For example, polymorphic purity of the Crystalline Form B may comprise at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50% of Crystalline Form B of Compound I-MsOH.

Crystalline Form C

In certain embodiments, methods of making Crystalline Form C of Compound I-MsOH (Crystalline Form C) are provided.

In one embodiment, the method of making Crystalline Form C comprises (a) filtering suspension of Crystalline Form B of Compound I-MsOH, and (b) drying the filtered product under vacuum, and breaking up product to dry at ambient conditions. In a particular embodiment, the suspension of Crystalline Form B of Compound I-MsOH is in acetone. In further embodiments, the Compound I-MsOH used in step (a) is amorphous. It has been found that this drying temperature of less than about 20° C. provides for the conversion of the isolated Crystalline Form B to Crystalline Form C while minimizing the formation of Crystalline Form A.

In one embodiment, the method of making Crystalline Form C comprises (a) filtering suspension of Crystalline Form B of Compound I-MsOH, and (b) drying the filtered product under vacuum, and breaking up the product and drying at less than 20° C. In another embodiment, the method of making Crystalline Form C comprises (a) filtering suspension of Crystalline Form B of Compound I-MsOH, and (b) drying the filtered product under vacuum, and breaking up product to freeze dry. In some embodiments, the method of making Crystalline Form C comprises (a) filtering suspension of Crystalline Form B of Compound I-MsOH, and (b) freeze drying the filtered product under vacuum.

In other embodiments, the Crystalline Form C prepared by the embodiments above is substantially pure. For example, polymorphic purity of the Crystalline Form C may comprise at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50% of Crystalline Form C of Compound I-MsOH.

Amorphous Materials

In one embodiment, the amorphous form of Compound I-MsOH exhibits a modulated DSC thermogram comprising a glass transition temperature at about 81.9° C. with the error of margin of about ±2.5; about ±2.0; about ±1.5; about ±1.0; about ±0.5; or less. In one specific embodiment, the amorphous of Compound I-MsOH exhibits a DSC thermogram that is substantially similar to FIG. 11.

In one specific embodiment, the amorphous of Compound I-MsOH exhibits an XRPD that is substantially similar to FIG. 10.

Methods of Making Amorphous Materials

In certain embodiments, methods of making a stable amorphous form of Compound I-MsOH are provided.

In one embodiment, the method of making amorphous Compound I-MsOH comprises (a) dissolving a Compound I-MsOH in a suitable solvent; (b) evaporating a portion of the suitable solvent from the solution of step (a); and (c) isolating an amorphous form of Compound I-MsOH. In further embodiments, the suitable solvent is selected from the group consisting of dichloromethane, tetrahydrofuran and methanol. In further embodiments, the evaporating step (b) is conducted under ambient conditions. In certain other further embodiments, the evaporating step (b) is conducted under pressure below that of atmospheric pressure (rotary evaporation).

In one embodiment, the method of making amorphous Compound I-MsOH comprises (a) dissolving a Compound I-MsOH in a suitable solvent; (b) freeze-drying solution of step (a); and (c) isolating an amorphous form of Compound I-MsOH. In further embodiments, the suitable solvent is tert-butanol/water.

Micronization of Crystalline Forms

In one embodiment, the present disclosure provides micronized Crystalline forms of Compound I-MsOH. In one embodiment, the Crystalline Form A of Compound I-MsOH is micronized. In one embodiment, the Crystalline Form B of Compound I-MsOH is micronized. In one embodiment, the Crystalline Form C of Compound I-MsOH is micronized.

As used herein, "$D_{90}$" of an indicated diameter means that 90% of the particles of a compound of the invention have a diameter that is less than the indicated diameter. For example, a $D_{90}$ of 7.6 μm means that 90% of the particles of a compound of the invention have a diameter that is less than 7.6 μm. Similarly, as used herein, "$D_{50}$" of an indicated diameter means that 50% of the particles of a compound of the invention have a diameter that is less than the indicated diameter. Also, as used herein, "$D_{10}$" of an indicated diameter means that 10% of the particles of a compound of the invention have a diameter that is less than the indicated diameter.

In some embodiments, the Crystalline forms of Compound I-MsOH have a $D_{90}$ ranging from about 1 μm to about 20 μm. In some embodiments, the Crystalline forms of Compound I-MsOH have a $D_{90}$ ranging from about 2 μm to about 15 μm. In other embodiments, the Crystalline forms of Compound I-MsOH have a $D_{90}$ ranging from about 3 μm to about 10 μm. In some embodiments, the Crystalline forms of Compound I-MsOH have a $D_{90}$ ranging from about 4 μm to about 9 μm.

In some embodiments, the Crystalline forms of Compound I-MsOH have a $D_{90}$ of about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, or about 25 μm, or a value ranging from and to any of these diameters. In some embodiments, the Crystalline forms of Compound I-MsOH have a $D_{90}$ of about 6.0 μm, about 6.1 μm, about 6.2 μm, about 6.3 μm, about 6.4 μm, about 6.5 μm, about 6.6 μm, about 6.7 μm, about 6.8 μm, about 6.9 μm, about 7.0 μm, about 7.1 μm, about 7.2 μm, about 7.3 μm, about 7.4 μm, about 7.5 μm, about 7.6 μm, about 7.7 μm, about 7.8 μm, about 7.9 μm, about 8.0 μm, 8.1 μm, about 8.2 μm, about 8.3 μm, about 8.4 μm, about 8.5 μm, about 8.6 μm, about 8.7 μm, about 8.8 μm, about 8.9 μm, or about 9.0 μm, or a value ranging from and to any of these diameters.

In some embodiments, the Crystalline forms of Compound I-MsOH have a $D_{50}$ ranging from about 0.5 μm to about 20 μm. In some embodiments, the Crystalline forms of Compound I-MsOH have a $D_{50}$ ranging from about 1 μm to about 15 μm. In other embodiments, the Crystalline forms of Compound I-MsOH have a $D_{50}$ ranging from about 1 μm to about 10 μm. In some embodiments, the Crystalline forms of Compound I-MsOH have a $D_{50}$ ranging from about 1 μm to about 5 μm.

In some embodiments, the Crystalline forms of Compound I-MsOH have a $D_{50}$ of about 0.5 μm, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, or about 25 μm, or a value ranging from and to any of these diameters. In some embodiments, the Crystalline forms of Compound I-MsOH have a $D_{50}$ of about 0.5 μm, about 0.6 μm, about 0.7 μm, about 0.8 μm, about 0.9 μm, about 1.0 μm, about 1.1 μm, about 1.2 μm, about 1.3 μm, about 1.4 μm, about 1.5 μm, about 1.6 μm, about 1.7 μm, about 1.8 μm, about 1.9 μm, about 2.0 μm, about 2.1 μm, about 2.2 μm, about 2.3 μm, about 2.4 μm, about 2.5 μm, about 2.6 μm, about 2.7 μm, about 2.8 μm, about 2.9 μm, about 3.0 μm, 3.1 μm, about 3.2 μm, about 3.3 μm, about 3.4 μm, about 3.5 μm, about 3.6 μm, about 3.7 μm, about 3.8 μm, about 3.9 μm, about 4.0 μm, 4.1 μm, about 4.2 μm, about 4.3 μm, about 4.4 μm, about 4.5 μm, about 4.6 μm, about 4.7 μm, about 4.8 μm, about 4.9 μm, or about 5.0 μm, or a value ranging from and to any of these diameters.

In some embodiments, the Crystalline forms of Compound I-MsOH have a $D_{10}$ ranging from about 0.1 μm to about 10 µm. In some embodiments, the Crystalline forms of Compound I-MsOH have a $D_{10}$ ranging from about 0.1 µm to about 5 µm. In other embodiments, the Crystalline forms of Compound I-MsOH have a $D_{10}$ ranging from about 0.1 µm to about 1 µm. In some embodiments, the Crystalline forms of Compound I-MsOH have a $D_{10}$ ranging from about 0.2 µm to about 0.8 µm.

In some embodiments, the Crystalline forms of Compound I-MsOH have a $D_{10}$ of about 0.1 µm, about 0.2 µm, about 0.3 µm, about 0.4 µm, about 0.5 µm, about 0.6 µm, about 0.7 µm, about 0.8 µm, about 0.9 µm, about 1 µm, about 2 µm, about 3 µm, about 4 µm, about 5 µm, about 6 µm, about 7 µm, about 8 µm, about 9 µm, or about 10 µm, or a value ranging from and to any of these diameters. In some embodiments, the Crystalline forms of Compound I-MsOH have a $D_{10}$ of about 0.1 µm, about 0.2 µm, about 0.3 µm, about 0.4 µm, 0.5 µm, about 0.6 µm, about 0.7 µm, about 0.8 µm, about 0.9 µm, about 1.0 µm, about 1.1 µm, about 1.2 µm, about 1.3 µm, about 1.4 µm, about 1.5 µm, about 1.6 µm, about 1.7 µm, about 1.8 µm, about 1.9 µm, or about 2.0 µm, or a value ranging from and to any of these diameters. In some embodiments, the Crystalline forms of Compound I-MsOH have a $D_{10}$ of about 0.41 µm, about 0.42 µm, about 0.43 µm, about 0.44 µm, about 0.45 µm, about 0.46 µm, about 0.47 µm, about 0.48 µm, about 0.49 µm, 0.50 µm, about 0.51 µm, about 0.52 µm, about 0.53 µm, about 0.54 µm, about 0.55 µm, about 0.56 µm, about 0.57 µm, about 0.58 µm, about 0.59 µm, about 0.60 µm, about 0.61 µm, about 0.62 µm, about 0.63 µm, about 0.64 µm, about 0.65 µm, about 0.66 µm, about 0.67 µm, about 0.68 µm, about 0.69 µm, about 0.70 µm, about 0.71 µm, about 0.72 µm, about 0.73 µm, about 0.74 µm, about 0.75 µm, about 0.76 µm, about 0.77 µm, about 0.78 µm, about 0.79 µm, or about 0.80 µm, or a value ranging from and to any of these diameters.

In some embodiments, the particle size and the particle size distribution (e.g., $D_{90}$, $D_{50}$, and $D_{10}$) of a compound of the invention is determined by the laser light diffraction particle size distribution analysis. The particle size distribution is determined in accordance with the Fraunhofer light diffraction method. In this method, a coherent laser beam passes through the sample and the resulting diffraction pattern is focused on a multi-element detector. Since the diffraction pattern depends, among other parameters, on particle size, the particle size distribution can be calculated based on the measured diffraction pattern of the sample. In one embodiment, the particle size and the particle size distribution is measured according to U.S. Pharmacopeia (USP) <429>.

In one embodiment, the micronized Crystalline forms of Compound I-MsOH have a surface area of about 5 $m^2/g$ to about 20 $m^2/g$. In another embodiment, the micronized Crystalline forms of Compound I-MsOH have a surface area of about 7 $m^2/g$ to about 18 $m^2/g$. In other embodiments, the micronized Crystalline forms of Compound I-MsOH have a surface area of about 8 $m^2/g$ to about 15 $m^2/g$. In some embodiments, the micronized Crystalline forms of Compound I-MsOH have a surface area of about 10 $m^2/g$ to about 14 $m^2/g$. In one embodiment, the micronized Crystalline forms of Compound I-MsOH have a surface area of about 12 $m^2/g$.

In one embodiment, the micronized Crystalline forms of Compound I-MsOH have a surface area of about 5 $m^2/g$, about 6 $m^2/g$, about 7 $m^2/g$, about 8 $m^2/g$, about 9 $m^2/g$, about 10 $m^2/g$, about 11 $m^2/g$, about 12 $m^2/g$, about 13 $m^2/g$, about 14 $m^2/g$, about 15 $m^2/g$, about 16 $m^2/g$, about 17 $m^2/g$, about 18 $m^2/g$, about 19 $m^2/g$, or about 20 $m^2/g$, or a value ranging from and to any of these surface areas. In one embodiment, the micronized Crystalline forms of Compound I-MsOH have a surface area of about 10.0 $m^2/g$, about 10.1 $m^2/g$, about 10.2 $m^2/g$, about 10.3 $m^2/g$, about 10.4 $m^2/g$, about 10.5 $m^2/g$, about 10.6 $m^2/g$, about 10.7 $m^2/g$, about 10.8 $m^2/g$, about 10.9 $m^2/g$, about 11.0 $m^2/g$, about 11.1 $m^2/g$, about 11.2 $m^2/g$, about 11.3 $m^2/g$, about 11.4 $m^2/g$, about 11.5 $m^2/g$, about 11.6 $m^2/g$, about 11.7 $m^2/g$, about 11.8 $m^2/g$, about 11.9 $m^2/g$, about 12.0 $m^2/g$, about 12.1 $m^2/g$, about 12.2 $m^2/g$, about 12.3 $m^2/g$, about 12.4 $m^2/g$, about 12.5 $m^2/g$, about 12.6 $m^2/g$, about 12.7 $m^2/g$, about 12.8 $m^2/g$, about 12.9 $m^2/g$, about 13.0 $m^2/g$, about 13.1 $m^2/g$, about 13.2 $m^2/g$, about 13.3 $m^2/g$, about 13.4 $m^2/g$, about 13.5 $m^2/g$, about 13.6 $m^2/g$, about 13.7 $m^2/g$, about 13.8 $m^2/g$, about 13.9 $m^2/g$, or about 14.0 $m^2/g$, or a value ranging from and to any of these surface areas. In one embodiment, the micronized Crystalline forms of Compound I-MsOH have a surface area of about 12.0 $m^2/g$, about 12.1 $m^2/g$, about 12.2 $m^2/g$, about 12.3 $m^2/g$, about 12.4 $m^2/g$, about 12.5 $m^2/g$, about 12.6 $m^2/g$, about 12.7 $m^2/g$, about 12.8 $m^2/g$, about 12.9 $m^2/g$, or about 13.0 $m^2/g$, or a value ranging from and to any of these surface areas.

In one embodiment, the micronized Crystalline forms of Compound I-MsOH have a tapped bulk density of about 0.05 to about 1.0. In another embodiment, the micronized Crystalline forms of Compound I-MsOH have a tapped bulk density of about 0.1 to about 0.5. In other embodiments, the micronized Crystalline forms of Compound I-MsOH have a tapped bulk density of about 0.15 to about 0.20.

In one embodiment, the micronized Crystalline forms of Compound I-MsOH have a tapped bulk density of about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, or about 0.60, or a value ranging from and to any of values.

Dissolution

In one embodiment, the present disclosure provides Crystalline forms of Compound I-MsOH which has an extrapolated intrinsic dissolution rate of about 1 µg/min to about 25 µg/min at about pH 3.1 to about pH 3.2. In another embodiment, the present disclosure provides Crystalline forms of Compound I-MsOH which has an extrapolated intrinsic dissolution rate of about 5 µg/min to about 15 µg/min. In one embodiment, the present disclosure provides Crystalline forms of Compound I-MsOH which has an extrapolated intrinsic dissolution rate of about 6 µg/min to about 12 µg/min. In one embodiment, the Crystalline Form A of Compound I-MsOH is micronized. In one embodiment, the Crystalline Form B of Compound I-MsOH is micronized. In one embodiment, the Crystalline Form C of Compound I-MsOH is micronized.

In one embodiment, the extrapolated intrinsic dissolution rate is measured using dissolution disc having 7.07 $mm^2$ which was compressed under high pressure, ca. 100 kg, using a constructed die. In one embodiment, a Sirius T3 was used as the dissolution apparatus containing 20 mL of test media with stirring speed of the paddle set to ~30%. In some embodiments, the dissolution was measured at room temperature. In one embodiment, dissolution was measured over 1 pH sector by ultraviolet (UV) spectrometry. In one embodiment, the UV spectra of the dissolution solution was collected over time, for example every 30 seconds, and converted to concentration using the molar extinction coefficient (MEC) by UV-metric titration. In one embodiment, the intrinsic dissolution rate was calculated by dividing the extrapolated dissolution rate by the surface area of the dissolution disc. In one embodiment, the dissolution media was Britton-Robinson buffer solution. In one embodiment, the dissolution media was pH 3.1 Britton-Robinson buffer solution. In one embodiment, the dissolution media was pH 3.2 Britton-Robinson buffer solution. In another embodiment, the dissolution media was pH 4.7 Britton-Robinson buffer solution.

In some embodiments, the Crystalline forms of Compound I-MsOH have an extrapolated intrinsic dissolution rate of about 1 µg/min, about 2 µg/min, about 3 µm µg/min, about 4 µg/min, about 5 µg/min, about 6 µg/min, about 7 µm µg/min about 8 µg/min, about 9 µg/min, about 10 µg/min, about 11 µg/min, about 12 µg/min, about 13 µg/min, about 14 µg/min, about 15 µg/min, about 16 µg/min, about 17 µg/min, about 18 µg/min, about 19 µg/min, about 20 µg/min, about 21 µg/min, about 22 µg/min, about 23 µg/min, about 24 µg/min, or about 25 µm µg/min or a value ranging from and to any of these dissolution rate at about pH 3.1 to about pH 3.2. In some embodiments, the Crystalline forms of Compound I-MsOH have an extrapolated intrinsic dissolution rate of about 4.0 µg/min, about 4.1 µg/min, about 4.2 µg/min, about 4.3 µg/min, about 4.4 µg/min, about 4.5 µg/min, about 4.6 µg/min, about 4.7 µg/min, about 4.8 µg/min, about 4.9 µg/min, about 5.0 µg/min, about 5.1 µg/min, about 5.2 µg/min, about 5.3 µg/min, about 5.4 µg/min, about 5.5 µg/min, about 5.6 µg/min, about 5.7 µg/min, about 5.8 µg/min, about 5.9 µg/min, about 6.0 µg/min, about 6.1 µg/min, about 6.2 µg/min, about 6.3 µg/min, about 6.4 µg/min, about 6.5 µg/min, about 6.6 µg/min, about 6.7 µg/min, about 6.8 µg/min, about 6.9 µg/min, about 7.0 µm µg/min, about 7.1 µg/min, about 7.2 µg/min, about 7.3 µg/min, about 7.4 µg/min, about 7.5 µg/min, about 7.6 µg/min, about 7.7 µg/min, about 7.8 µg/min, about 7.9 µg/min, about 8.0 µg/min, about 8.1 µg/min, about 8.2 µg/min, about 8.3 µg/min, about 8.4 µg/min, about 8.5 µg/min, about 8.6 µg/min, about 8.7 µg/min, about 8.8 µg/min, about 8.9 µg/min, about 9.0 µg/min, about 9.1 µg/min, about 9.2 µg/min, about 9.3 µg/min, about 9.4 µg/min, about 9.5 µg/min, about 9.6 µg/min, about 9.7 µg/min, about 9.8 µg/min, about 9.9 µg/min, about 10.0 µg/min, about 10.1 µg/min, about 10.2 µg/min, about 10.3 µg/min, about 10.4 µg/min, about 10.5 µg/min, about 10.6 µg/min, about 10.7 µg/min, about 10.8 µg/min, about 10.9 µg/min, about 11.0 µg/min, about 11.1 µg/min, about 11.2 µg/min, about 11.3 µg/min, about 11.4 µg/min, about 11.5 µg/min, about 11.6 µg/min, about 11.7 µg/min, about 11.8 µg/min, about 11.9 µg/min, about 12.0 µg/min, about 12.1 µg/min, about 12.2 µg/min, about 12.3 µg/min, about 12.4 µg/min, about 12.5 µg/min, about 12.6 µg/min, about 12.7 µg/min, about 12.8 µg/min, about 12.9 µg/min, about 13.0 µg/min, about 13.1 µg/min, about 13.2 µg/min, about 13.3 µg/min, about 13.4 µg/min, about 13.5 µg/min, about 13.6 µg/min, about 13.7 µg/min, about 13.8 µg/min, about 13.9 µg/min, or about 14.0 µg/min, or a value ranging from and to any of these dissolution rate at about pH 3.1 to about pH 3.2.

In some embodiments, the Crystalline forms of Compound I-MsOH have an extrapolated intrinsic dissolution rate of about 6.5 µg/min to about 12.0 µg/min at about pH 3.1 to about pH 3.2. In other embodiments, the Crystalline forms of Compound I-MsOH have an extrapolated intrinsic dissolution rate of about 6.5 µg/min to about 11.0 µg/min at about pH 3.1 to about pH 3.2. In other embodiments, the Crystalline forms of Compound I-MsOH have an extrapolated intrinsic dissolution rate of about 6.5 µg/min to about 10.0 µg/min at about pH 3.1.

Pharmaceutical Compositions

In one embodiment, the present invention provides a pharmaceutical composition comprising a crystalline polymorphic form or an amorphous form of CVC mesylate and a pharmaceutically acceptable excipient. As used herein, a "pharmaceutically acceptable excipient" includes without limitation any adjuvant, carrier, glidant, sweetening agent, diluent, preservative, dye/colorant, flavor enhancer, surfactant, wetting agent, dispersing agent, suspending agent, stabilizer, bulking agent, fillers, isotonic agent, solvent, or emulsifier which has been approved by the United States Food and Drug Administration as being acceptable for use in humans or domestic animals. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In one aspect, the present invention provides a pharmaceutical composition and a combination package that are useful for treating fibrosis and/or fibrotic diseases or conditions.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

In one embodiment, the pharmaceutical composition comprises a therapeutically effective amount of (a) an additional therapeutic agent; and (b) a CVC mesylate or solvate thereof. Ingredients (a) and (b) are pharmaceutically active ingredients. The pharmaceutical composition may comprise additional active ingredients besides (a) and (b). For example, the pharmaceutical composition may comprise the additional active agent as described above. In one embodiment, the additional active agent is a FXR or PPAR-α agonist. In one embodiment, the additional active agent is a chemokine antagonist.

In one specific embodiment, the pharmaceutical composition comprises a FXR agonist and CVC mesylate or a solvate thereof. In another specific embodiment, the pharmaceutical composition comprises a PPAR-α agonist and CVC mesylate or a solvate thereof. In one specific embodiment, the pharmaceutical composition comprises a chemokine antagonist and CVC mesylate or a solvate thereof.

In further embodiments, the CVC mesylate ingredient (b) is Crystalline Form A, Crystalline Form B, Crystalline Form C, or amorphous, or mixtures thereof.

In one embodiment, the pharmaceutical composition comprises a therapeutically effective amount of CVC mesylate or solvate thereof. In further embodiments, the CVC mesylate is Crystalline Form A, Crystalline Form B, Crystalline Form C, or amorphous, or mixtures thereof.

The CVC mesylate or solvate thereof may be formulated into any dosage form suitable for oral or injectable administration. When the compound is administered orally, it can be formulated into solid dosage forms for oral administration, for example, tablets, capsules, pills, granules, and so on. It also can be formulated into liquid dosage forms for oral administration, such as oral solutions, oral suspensions, syrups and the like. The term "tablets" as used herein, refers to those solid preparations which are prepared by homogeneously mixing and pressing the compounds and suitable auxiliary materials into circular or irregular troches, mainly in common tablets for oral administration, including also buccal tablets, sublingual tablets, buccal wafer, chewable tablets, dispersible tablets, soluble tablets, effervescent tablets, sustained-release tablets, controlled-release tablets, enteric-coated tablets and the like. The term "capsules" as used herein, refers to those solid preparations which are prepared by filling the compounds, or the compounds together with suitable auxiliary materials into hollow capsules or sealing into soft capsule materials. According to the solubility and release property, capsules can be divided into hard capsules (regular capsules), soft capsules (soft shell capsules), sustained-release capsules, controlled-release capsules, enteric-coated capsules and the like. The term "pills" as used herein, refers to spherical or near-spherical solid preparations which are prepared by mixing the compounds and suitable auxiliary materials via suitable methods, including dropping pills, dragee, pilule and the like. The term "granules" as used herein, refers to dry granular preparations which are prepared by mixing the compounds and suitable auxiliary materials and have a certain particle size. Granules can be divided into soluble granules (generally referred to as granules), suspension granules, effervescent granules, enteric-coated granules, sustained-release granules, controlled-release granules and the like. The term "oral solutions" as used herein, refers to a settled liquid preparation which is prepared by dissolving the compounds in suitable solvents for oral administration. The term "oral suspensions" as used herein, refers to suspensions for oral administration, which are prepared by dispersing the insoluble compounds in liquid vehicles, also including dry suspension or concentrated suspension. The term "syrups" as used herein, refers to a concentrated sucrose aqueous solution containing the compounds. The injectable dosage form can be produced by the conventional methods in the art of formulations, and aqueous solvents or non-aqueous solvents may be selected. The most commonly used aqueous solvent is water for injection, as well as 0.9% sodium chloride solution or other suitable aqueous solutions. The commonly used non-aqueous solvent is vegetable oil, mainly soy bean oil for injection, and others aqueous solutions of alcohol, propylene glycol, polyethylene glycol, and etc.

In one embodiment, a pharmaceutical composition comprising a crystalline Form of CVC mesylate and fumaric acid is provided. In further embodiment the CVC mesylate is Crystalline Form A. In further embodiment the CVC mesylate is Crystalline Form C.

In further embodiments, the weight ratio of CVC mesylate to fumaric acid is from about 7:10 to about 10:7, such as from about 8:10 to about 10:8, from about 9:10 to about 10:9, or from about 95:100 to about 100:95. In other further embodiments, the fumaric acid is present in an amount of from about 15% to about 40%, such as from about 20% to about 30%, or about 25%, by weight of the composition. In other further embodiments, CVC mesylate thereof is present in an amount of from about 15% to about 40%, such as from about 20% to about 30%, or about 25%, by weight of the composition.

Methods of Use

In one aspect, the present invention provides methods of treating fibrosis or a fibrotic disease or condition in a subject in need thereof comprising administering to the subject a therapeutically effective amount of a crystalline polymorphic form, or amorphous form, of CVC mesylate, or solvate thereof. In further embodiments, the crystalline polymorphic form of CVC mesylate comprises Crystalline Form A, Crystalline Form B, Crystalline Form C or mixtures thereof.

In another embodiment, the fibrosis or fibrotic disease or condition is liver fibrosis or renal fibrosis. In yet a further embodiment, the liver fibrosis is associated with non-alcoholic steatohepatitis (NASH). In yet a further embodiment, the liver fibrosis is associated with non-alcoholic fatty liver disease (NAFLD). In yet a further embodiment, the liver fibrosis is associated with emerging cirrhosis. In another further embodiment, the liver fibrosis comprises non-cirrhotic hepatic fibrosis. In a further embodiment, the subject is infected by human immunodeficiency virus (HIV). In a further embodiment, the cenicriviroc or a salt or solvate thereof is formulated as a pharmaceutical composition comprising cenicriviroc or a salt or solvate thereof and fumaric acid. In a further embodiment, the subject has a disease or condition selected from the group consisting of alcoholic liver disease, HIV and HCV co-infection, HCV infection, type 2 diabetes mellitus (T2DM), metabolic syndrome (MS), and a combination thereof.

In one embodiment, the invention provides a method of treating fibrosis or a fibrotic disease or condition or condition in a subject in need thereof comprising co-administering to the subject a therapeutically effective amount of a crystalline polymorphic form, or amorphous form, of CVC mesylate; and one or more additional active agents. In a further embodiment, the additional active agent is selected from the group consisting of a GLP-1 receptor agonist, a SGLT2 inhibitor, a DPP-4 inhibitor, an inhibitor of Toll-Like Receptor 4 signaling, an anti-TGFβ antibody, a thiazolidinedione, a PPAR subtypes α and γ agonist, and an oral insulin sensitizer. In another further embodiment, the additional active agent is selected from the group consisting of liraglutide, evogliptin, canagliflozin, anagliptin, TAK-242, 1D11, MSDC-0602, pioglitazone, and rosiglitazone.

EXAMPLES

The present invention is further illustrated by reference to the following Examples. However, it is noted that these Examples, like the embodiments described above, are illustrative and are not to be construed as restricting the scope of the invention in any way.

"EtOAc" means ethyl acetate. "EtOH" means ethanol. "ACN" means acetonitrile. "MIBK" means methyl isobutylketone. "TBME" means methyl tert-butyl ether. "IPA" means isopropyl alcohol. "DCM" means dichloromethane. "THF" means tetrahydrofuran. "DME" means 1,2-dimethoxyethane. "MEK" means methyl ethyl ketone. "MeOH" means methanol. "IPAC" means isopropyl acetate.

X-Ray Powder Diffraction patterns were collected on: (1) a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate). The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically, the sample would be exposed to the X-ray beam for 120 seconds. The software used for data collection was GADDS for XP/2000 4.1.43 and the data were analyzed and presented using Diffrac Plus EVA v15.0.0.0; or (2) a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1. The data were analyzed and presented using Diffrac Plus EVA v15.0.0.0. Samples were run under ambient conditions as flat plate specimens using powder as received. The sample was gently packed into a cavity cut into polished, zero-background (510) silicon wafer. The sample was rotated in its own plane during analysis. The details of the data collection are: angular range of 2 to 42° 2θ, step size of 0.05° 2θ, collection time of 0.5 s/step.

DSC data were collected on a TA Instruments Q2000 equipped with a 50 position auto-sampler. The calibration for thermal capacity was carried out using sapphire and the calibration for energy and temperature was carried out using certified indium. Typically, 0.5-3 mg of each sample, in a pin-holed aluminum pan, was heated at 10° C./min from 25° C. to 300° C. A purge of dry nitrogen at 50 ml/min was maintained over the sample. Modulated temperature DSC was carried out using an underlying heating rate of 2° C./min and temperature modulation parameters of ±0.64° C. (amplitude) every 60 seconds (period). The instrument control software was Advantage for Q Series v2.8.0.394 and Thermal Advantage v5.5.3. The data were analyzed using Universal Analysis v4.5A.

TGA data were collected on a TA Instruments Q500 TGA, equipped with a 16 position auto-sampler. The instrument was temperature calibrated using certified Alumel and Nickel. Typically, 5-10 mg of each sample was loaded onto a pre-tared aluminum DSC pan and heated at 10° C./min from ambient temperature to 350° C. A nitrogen purge at 60 ml/min was maintained over the sample. The instrument control software was Advantage for Q Series v2.5.0.256 and Thermal Advantage v5.5.3. The data were analyzed using Universal Analysis v4.5A.

Solid State NMR spectra were acquired on a Bruker Avance III console using a widebore Bruker 4 mm BB/1H WVT Magic Angle Spinning (MAS) probe and TopSpin 3.1 software at a static magnetic field strength of 9.4 T (ν0(1H)=400.16 MHz). For $^{13}C$, the probe was tuned to 100.63 MHz and the spectra referenced to the alanine CH3 signal at 20.5 ppm. For $^{15}N$, the probe was tuned to 40.55 MHz and the spectra referenced to glycine at −347.4 ppm. Powdered samples were packed into zirconia MAS rotors with KelF caps, with before and after weighing providing the sample mass. The rotors were spun using room-temperature purified compressed air. All spectra were recorded using cross polarization (CP), in which magnetization is transferred from $^1H$ to either $^{13}C$ or $^{15}N$ nuclei via the dipolar coupling (i.e. a through-space rather than through-bond interaction). This method enhances the observed signal, and significantly reduces the time taken to record a spectrum. A contact time of 1 ms was used for the $^{13}C$ experiments, and 1.5 ms for the $^{15}N$ experiments. High power (100 W) SPINAL-64 decoupling was applied to the $^1H$ channel during acquisition. Experimental parameters for solid-state MAS NMR experiments shown below:

| Sample | Experiment | MASR (Hz) | D1 (s) | Scans | Mass (mg) | LB (Hz) |
|---|---|---|---|---|---|---|
| Form A | 13C | 10000 | 3 | 1296 | 45.9 | 12 |
|  | 15N | 10000 | 3 | 24600 | 62.6 | 25 |
| Form C | 13C | 10000 | 3 | 3216 | 45.9 | 12 |
|  | 15N | 10000 | 3 | 26224 | 62.6 | 25 |

Data were collected on a Phenom Pro Scanning Electron Microscope. A small quantity of sample was mounted onto an aluminum stub using conducting double-sided adhesive tape. A thin layer of gold was applied using a sputter coater (20 mA, 120 s).

Example 1: Preparation of Crystalline Form A

Substantially pure Form A may be prepared from amorphous CVC Mesylate using various crystallizations methods. Exemplary methods are provided below.

Slurry at 5° C.:

Amorphous CVC Mesylate (~40 mg) was cooled to 5° C. and portions of chilled solvent (or solvent mixtures) (about 100 µL of solvent) were added to form a slurry. The slurry was stirred at 5° C. for 1 hour and then, if needed, additional portions of solvent were added (for example, if the suspension could not be stirred). The slurry was stirred overnight at 5° C. The sample was air dried on the XRPD silicon sample wafer, and the polymorphic form of the sample was tested using XRPD analysis.

Slurrying amorphous CVC Mesylate in following solvents (or solvent mixtures) at 5° C. provides Form A: EtOAc, IPAC, MIBK, IPA, EtOH, 2-methyl-1-propanol, propyl acetate, ACN, 1,2-DME, nitromethane, EtOAc:ACN (1:1), EtOAc:ACN:water (9.5:9.5:1), EtOAc:ACN:pyridine (9.5:9.5:1), EtOAc:ACN:DCM (9.5:9.5:1), ACN:EtOAc (95:5), ACN:pyridine (95:5) and ACN:DCM (95:5) (solvent mixtures are v/v).

Slurry at 50° C.:

Amorphous CVC Mesylate (~40 mg) was warmed to 50° C. and portions of warm solvent (or solvent mixtures) (about 100 µL of solvent) were added to form a slurry. The slurry was stirred at 50° C. for 1 hour and then, if needed, additional portions of solvent were added (for example, if the suspension could not be stirred). The slurry was stirred overnight at 50° C. The sample was air dried on the XRPD silicon sample wafer, and the polymorphic form of the sample was tested using XRPD analysis.

Slurrying amorphous CVC Mesylate in following solvents (or solvent mixtures) at 50° C. provides Crystalline Form A: EtOAc, IPAC, MIBK, IPA, MEK, acetone, TBME, propyl acetate, anisole, toluene, ACN, 1,2-DME, EtOAc:ACN (1:1), EtOAc:ACN:pyridine (9.5:9.5:1), EtOAc:ACN:DCM (9.5:9.5:1), ACN:EtOAc (95:5), ACN:pyridine (95:5) and ACN:DCM (95:5) (solvent mixtures are v/v).

Maturation of a Slurry Between 25 and 50° C.:

Amorphous CVC Mesylate (~40 mg) was warmed to 50° C. and portions of solvent (or solvent mixtures) was added to form mobile slurries. Samples were stirred at 50° C. for 1 hour, additional portions of solvent were added as required (where the sample consisted of a very thick suspension or had become solid). Samples were maturated overnight (which consisted of stirring cycles of 4 hours at 25° C. then 4 hours at 50° C.). Confirmation of the solid form was carried out using XRPD analysis.

The following solvents may be employed in this procedure to provide Form A: EtOAc, IPAC, MIBK, IPA, EtOH, and 2-methyl-1-propanol, Anti-Solvent Addition:

Solutions (~40 mg CVC Mesylate in 100 µl solvent) were stirred at 25° C. and 100 µl aliquots of anti-solvent was added, with approximately 1 hour stirring between additions. Anti-solvent was added until a solid or oil precipitated. A solution of CVC Mesylate in methanol with TBME as an anti-solvent gave a solid precipitate, all other solvent/anti-solvent combinations listed in the table formed oils. The oils were left to stir at 25° C. for 3 days, after which a solid precipitate had formed. Confirmation of the solid form was carried out using XRPD analysis.

Evaporation:

Solutions of CVC Mesylate were left at ambient conditions to evaporate slowly via loosened lids. Suspensions were formed upon partial evaporation of the liquors. Confirmation of the solid form was carried out using XRPD analysis.

Solvent Drop Grinding:

Solvent (10 µl) and two 3 mm stainless steel ball bearings were added to amorphous CVC Mesylate (~40 mg). The samples were milled in a Fritsch Planetary mill for 2 hours at 650 rpm. After milling, the warm samples were allowed to cool to room temperature. Confirmation of the solid form was carried out using XRPD analysis.

Example 2: Preparation of Crystalline Form B

Slurries containing substantially pure Form B may be prepared from amorphous CVC Mesylate. Exemplary methods are provided below.

Amorphous CVC Mesylate (~40 mg) was equilibrated at 25 or 5° C. Solvent (100 µl of MEK, acetone or THF) was added, forming a gummy solid, which dissolved on stirring. Samples were left stirring at either 25 or 5° C. After 1 hour additional solvent (200 µl) was added to the samples slurried in acetone due to the formation of thick suspensions. The samples in THF had formed solutions and the sample in MEK had formed a gel. Samples were left to stir at 25 or 5° C. for 3 days, after which all samples had formed suspensions. The material was isolated by filtration under suction. Confirmation of the solid form was carried out using XRPD analysis.

Solutions of CVC Mesylate in DCM (~40 mg in 100 µl) were equilibrated at 5 or 25° C. n-Heptane anti-solvent (200 µl) was added forming a precipitate, which converted to a gummy solid on stirring. The samples were left to stir at 25 or 5° C. for 3 days, after which the samples formed a suspension. The material was isolated by filtration under suction. Confirmation of the solid form was carried out using XRPD analysis.

Example 3: Preparation of Crystalline Form C

Substantially pure Form C may be prepared from amorphous CVC Mesylate. Exemplary methods are provided below.

Amorphous CVC Mesylate (~3 g) was dissolved in acetone (7.5 ml, 2.5 volumes); initially a gummy solid formed which dissolved on stirring at 25° C. After approximately 50 minutes stirring, the solution became cloudy and the sample was seeded with Form C material, a few minutes later a large amount of yellow precipitate was observed. After a further 10 minutes of stirring, more acetone (15 ml, 5 volumes) was added to maintain a mobile slurry. After a total of 2 hours stirring, a further portion of acetone (15 ml, 5 volumes) was added as the suspension had become very thick. After a total of 6 hours stirring a further portion of acetone (15 ml, 5 volumes) was added as the suspension had become very thick again. The sample was left to stir for 4 days at 25° C. (300 rpm).

After stirring for 4 days, the sample was a thick suspension but was mobile and slowly stirring. The suspension was filtered through a 0.45 µm PTFE filter, and washed with the filtrate until the liquors became clear. The sample was air dried (under suction) at ambient conditions for approximately 30 minutes. The yield after 30 minutes air drying was 2.9575 g, 98.5 wt %. The cake was broken up into a powder and was left at ambient conditions to dry naturally overnight. Confirmation of the solid form was carried out using XRPD analysis.

Example 4: Preparation of Stable Amorphous Compound I-MsOH

Stable amorphous Compound I-MsOH may be prepared from Crystalline Form A of Compound I-MsOH. Exemplary methods are provided below.

Evaporation at Ambient Conditions:

CVC Mesylate (Form A) was dissolved in DCM (12.5 volumes, 80 mg/ml), forming a clear yellow stock solution. The stock solution (0.5 ml, containing 40 mg CVC Mesylate) was pipetted into glass HPLC vials and the samples were left uncapped to evaporate at ambient conditions. Samples were then dried in a vacuum oven at room temperature. For each batch of samples prepared, a spare sample was made and this spare sample was analysed by XRPD, 1H NMR and HPLC. The evaporation and the vacuum oven drying times for each batch of samples were varied to reduce the DCM content of the amorphous material. An example list of evaporation and drying times is given in Table 4.

TABLE 4

Exemplary evaporation and drying times for the preparation of amorphous CVC mesylate by evaporation at ambient conditions

| Batch | Evaporation Time (days) | Drying time in vacuum oven (hours) | DCM content (determined by $^1$H NMR analysis |
|---|---|---|---|
| 1 | 1 | 3 | 0.60 mole eq, 6.0 wt % |
| 2 | 4 | 4 | 0.20 mole eq, 2.1 wt % |
| 3 | 2 | 4.5 | 0.16 mole eq, 1.6 wt % |
| 4 | 2 | 4 | 0.32 mole eq, 3.3 wt % |
| 5 | 1 | 5 | 0.26 mole eq, 2.7 wt % |

Rotary Evaporation:

CVC Mesylate (Form A, ~2 g) was dissolved in DCM (20 ml, 10 volumes), forming a clear yellow solution. The solvent was removed by rotary evaporation and the sample was dried on the rotary evaporator (approximately 2 mbar) for 6 hours with the bath at room temperature. The sample was dried further in a vacuum oven at room temperature overnight. The resulting yellow glassy material was analyzed by XRPD, $^1$H NMR and HPLC.

Freeze Drying:

CVC Mesylate (Form A, ~50 mg) was weighed into a round bottomed flask and dissolved in t-butanol/water (50/50 v/v, 4 ml). The sample was warmed to 60° C. to ensure complete dissolution had been achieved. The sample was flash frozen in dry ice/acetone (−78° C.) and was freeze dried overnight. The resulting material was a light fluffy yellow solid, which was analyzed by XRPD and $^1$H NMR.

Example 5: Physical Characteristics of CVC Polymorph Samples

Micronized CVC mesylate Form A, non-micronized CVC mesylate Form A and CVC mesylate Form C were prepared. CVC mesylate Form C used in this study was not micronized.

Particle Size: The particle size of the Micronized CVC mesylate Form A and the non-micronized CVC mesylate Form A were determined according to USP <429> as shown in Table 5.

TABLE 5

Particle Size (μm)

| | Form A Micronized | Form A Non-micronized |
|---|---|---|
| $D_{10}$ | 0.582 | 4.725 |
| $D_{50}$ | 3.226 | 13.803 |
| $D_{90}$ | 7.576 | 65.910 |

Tapped Bulk Density: Tapped bulk density analysis was performed by pouring powder that had been sieved through a 1 mm Retsch stainless steel test sieve into a clean, dry pre-weighed 50 ml measuring cylinder. Powder was added to a total volume of 45-50 ml without compacting the sample. The mass and the initial volume ($V_0$) were recorded. The sample was tapped using a Copley JV2000 tapped density tester using the following number of taps: 10, 490, 750 and sets of 1250 taps up to a total of 10,000 taps (Table 6). The volume was recorded after each set of taps and the sample was tapped until it reached constant volume ($V_f$). For these samples the 10,000 tap volume was used as $V_f$.

TABLE 6

Experimental Parameters for Tap Bulk Density Measurement

Number of taps

| Incremental | Total | Volume |
|---|---|---|
| 0 | 0 | $V_0$ |
| 10 | 10 | $V_{10}$ |
| 490 | 500 | $V_{500}$ |
| 750 | 1250 | $V_{1250}$ |
| 1250 | 2500 | $V_{2500}$ |
| 1250 | 3750 | $V_{3750}$ |
| 1250 | 5000 | $V_{5000}$ |
| 1250 | 6250 | $V_{6250}$ |
| 1250 | 7500 | $V_{7500}$ |
| 1250 | 8750 | $V_{8750}$ |
| 1250 | 10000 | $V_{10000}$ |

Each sample was analysed in duplicate and the tapped density, compressibility index (Carr's index) and Hausner ratios were calculated using the formulae given below. The results from the duplicate analysis were averaged and the average result was used to assess the flow properties of the sample, using the parameters given in Table 7 (see "The Science of Dosage Form Design", ME Aulton, 1988) and Table 8 (see USP method <1174>; see also, Carr, R. L. Evaluating Flow Properties of Solids. *Chem Eng.* 1965, 72, 163-168).

Tapped Bulk Density=$M/V_f$.

$$\text{Compressibility Index (Carr's Index)} = \frac{100\,(V_0 - V_f)}{V_0}$$

$$\text{Hausner ratio} = \frac{V_0}{V_f}$$

TABLE 7

Interpretation of Compressibility Index

| Compressibility Index (Carr's Index) | Flow Characteristics |
|---|---|
| 5-15 | Excellent |
| 12-16 | Good |
| 18-21 | Fair |
| 23-35 | Poor |
| 35-38 | Very poor |
| >40 | Extremely poor |

TABLE 8

Alternative Interpretation of Compressibility Index and Hausner Ratio

| Compressibility Index (Carr's Index) | Flow Character | Hausner Ratio |
|---|---|---|
| <10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very, poor | 1.46-1.59 |
| >38 | Very, very poor | >1.60 |

The tapped bulk density and flow characteristics determined for the samples are as shown in Table 9.

TABLE 9

Comparison of Tapped Bulk Density Results and Flow Characteristics

| Form | Rep. | Tapped Bulk Density | Compressibility (Carr's) Index | Hausner Ratio | Interpretation (flow) |
|---|---|---|---|---|---|
| Form A Micronised. | 1 | 0.16 | 27.55 | 1.42 | Poor |
|  | 2 | 0.16 | 29.59 | 1.40 |  |
|  | Mean | 0.2 | 28.6 | 1.4 |  |
| Form A Non-micronised. | 1 | 0.22 | 34.34 | 1.52 | Very Poor |
|  | 2 | 0.21 | 36.36 | 1.57 |  |
|  | Mean | 0.2 | 35.4 | 1.5 |  |
| Form C | 1 | 0.49 | 7.07 | 1.08 | Excellent |
|  | 2 | 0.48 | 5.00 | 1.05 |  |
|  | Mean | 0.5 | 6.0 | 1.1 |  |

Tapped Bulk Density = $M/V_f$;
$V_f$ = volume after 10,000 taps

Flow Properties: The flow properties of the samples were analysed using a Revolution Powder Analyser. Approximately 100 ml of the sample is placed in a sample drum which has two borosilicate glass sides. A motor turns two high precision silicone rollers, which in turn rotate the drum. A digital camera with the assistance of cold cathode backlight illumination takes images of the powder during the rotation process. Using a drum rotation speed of 0.3 rpm the time to avalanche, avalanche angle, avalanche energy, break energy and rest angle are measured. The software calculates these properties by analysing the images produced as the drum is rotated. The results of these properties can be used to assess the flow of the bulk powder. The interpretation of the rest angle (angle of repose) are given in Table 10 (see USP method <1174>; see also, Carr, R. L. Evaluating Flow Properties of Solids. *Chem Eng.* 1965, 72, 163-168).

TABLE 10

Interpretation of Rest Angle Data

| Flow Property | Rest Angle (degrees) |
|---|---|
| Excellent | 25-30 |
| Good | 31-35 |
| Fair - aid not needed | 36-40 |
| Passable - may hang up | 41-45 |
| Poor - must agitate, vibrate | 46-55 |
| Very poor | 56-65 |
| Very, very poor | >66 |

Summary of key parameters from Revolution Analyzer for flowability measurements are shown in Table 11. These results show that Form C is more dense and flows better than the Form A samples as the avalanche time, angle of avalanche and the avalanche energy are all significantly smaller for Form C than for the Form A samples. However, the rest angle is only slightly smaller leading to the same interpretation for micronized Form A and Form C, although the rest angles are at either extreme of the limits for a passable flow (41-45°).

TABLE 11

Summary of Parameters from Flowability Measurement

| Form | Form A Micronised | Form A Non-micronised | Form C |
|---|---|---|---|
| Sample Weight (g) | 13.25 | 15.85 | 41.80 |
| Sample Volume (cc) | 107.1 | 90.9 | 104.2 |
| Avalanche Time (sec) | 7.4 | 6.5 | 4.4 |
| Avalanche Energy (kJ/kg) | 32.98 | 41.58 | 20.28 |
| Avalanche Angle (deg) | 68.05 | 72.60 | 51.55 |
| Break Energy (kJ/kg) | 86.41 | 138.38 | 71.90 |
| Rest Angle (deg) | 44.85 | 50.75 | 41.30 |
| Interpretation (flow) | Passable | Poor | Passable |

Surface area: Surface Area was also determined for each samples as shown in Table 12. Samples were analysed for BET (Brunauer-Emmett-Teller) surface area by a multipoint Nitrogen adsorption method (volumetric technique) using a Micromeritics TriStar 3020 instrument.

The sample degassing was undertaken using a Micromeritics FlowPrep 060 applying flowing argon of 99.995% purity at a flow rate of approximately 20 cc/min for two hours at 20° C. Samples were degassed in their respective analysis tubes and transferred directly to the TriStar II immediately after the degassing period.

TABLE 12

Summary of Surface Area

| Form | Surface area (m$^2$/g) | BET constant, C |
|---|---|---|
| Form A Micronised | 12.3614 ± 0.0440 | 37.98 |
| Form A Non-micronised | 3.0295 ± 0.0122 | 42.99 |
| Form C | 2.3071 ± 0.0058 | 39.87 |

Intrinsic Dissolution: Appropriate weight of the pure test compound material were used to fill the cavity of the dissolution disc and compressed under high pressure, ca. 100 kg, using a constructed die. No additives were added, avoiding any external interference in the intrinsic dissolution profile. The resulting non-disintegrating disc was transferred to the dissolution apparatus, Sirius T3, containing 20 ml of the test media at room temperature. The stirring speed of the paddle was set to −30%. Dissolution was then measured over 1 pH sector. The solution spectra was collected every 30 seconds over 120 collection points and converted to concentration using the molar extinction coefficient (MEC) by UV-metric titration. Intrinsic dissolution rate was calculated by dividing the extrapolated dissolution rate by the surface area of the disk (7.07 mm$^2$). All analysis was performed in duplicate, with XRPD both prior to and post dissolution analysis, where possible. The observed dissolution rate for CVC mesylate micronized Form A and CVC Mesylate Form C as shown in Table 13.

Dissolution media, Britton-Robinson buffer solutions, were prepared by adding a specified volume of sodium hydroxide (0.2 M) to 200 ml of a solution of mixed acid, of 0.04 M with respect to phosphoric acid (2.72 ml/l), acetic acid (2.30 ml/l) and boric acid (2.476 g/l). The amount of sodium hydroxide used to prepare each buffer is outlined below:

pH 3.2 Britton-Robinson buffer: 38 ml of sodium hydroxide.

pH 4.7 Britton-Robinson buffer: 60 ml of sodium hydroxide

TABLE 13

Dissolution of CVC Mesylate micronized Form A and CVC Mesylate Form C

| | Form A | | Form C | |
|---|---|---|---|---|
| | Disc 1 | Disc 2 | Disc 1 | Disc 2 |
| Extrapolated Dissolution Rate (µg/min) | 7.20 | 9.43 | 10.80 | 11.38 |
| Average pH | 3.12 | 3.12 | 3.14 | 3.15 |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A crystalline form of

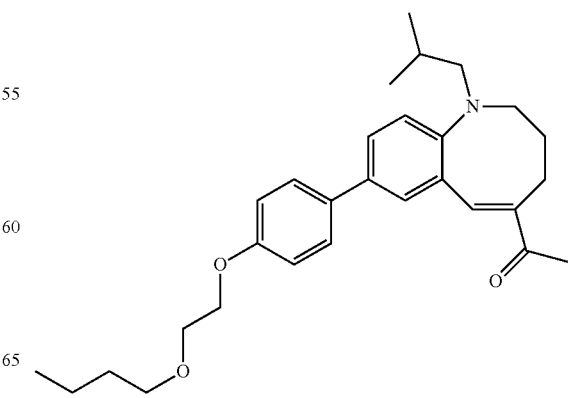

-continued

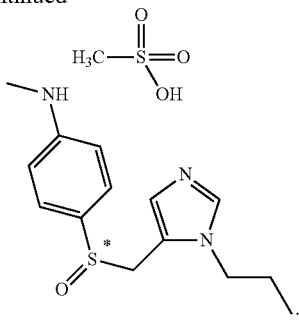

(Compound I—MsOH)

wherein the crystalline form is:
(a) crystalline form A which has an X-ray powder diffraction pattern with characteristic peaks expressed in values of degrees 2Θ at about 4.0±0.2, about 18.7±0.2, about 19.1±0.2, about 20.1±0.2 and about 21.7±0.2;
(b) crystalline form B which has an X-ray powder diffraction pattern with characteristic peaks expressed in values of degrees 2Θ at about 4.0±0.2, about 15.9±0.2, about 17.8±0.2, about 19.9±0.2, about 20.1±0.2, about 21.5±0.2 and about 21.6±0.2; or
(c) crystalline form C which has an X-ray powder diffraction pattern with characteristic peaks expressed in values of degrees 2Θ at about 4.0±0.2, about 10.0±0.2, about 16.0±0.2, about 18.7±0.2, about 20.0±0.2 and about 21.7±0.2.

2. The Crystalline Form A of claim 1, wherein the X-ray powder diffraction pattern further comprises characteristic peaks expressed in values of degrees 2Θ at about 10.0±0.2, about 17.4±0.2, about 20.4±0.2, about 20.7±0.2, and about 23.2±0.2.

3. The Crystalline Form A of claim 1, which exhibits a differential scanning calorimetry thermogram having a peak characteristic value at about 152.9±2.0° C.

4. The Crystalline Form A of claim 1, which exhibits a differential scanning calorimetry thermogram pattern substantially similar to FIG. 2; or exhibits a thermogravimetric analysis thermogram substantially similar to FIG. 3.

5. The Crystalline Form A of claim 1 with a polymorphic purity of at least about 50%.

6. The Crystalline Form A of claim 1 with a polymorphic purity of at least about 95%.

7. The Crystalline Form A of claim 1, having a $D_{90}$ ranging from about 5 μm to about 10 μm.

8. A pharmaceutical composition comprising the Crystalline Form A of claim 1 and a pharmaceutically acceptable excipient.

9. The Crystalline Form B of claim 1, wherein the X-ray powder diffraction pattern further comprises characteristic peaks expressed in values of degrees 2Θ at about 6.3±0.2, about 9.9±0.2, about 18.6±0.2, about 20.4±0.2 and about 21.1±0.2.

10. The Crystalline Form B of claim 1 with a polymorphic purity of at least about 50%.

11. The Crystalline Form B of claim 1, having a $D_{90}$ ranging from about 5 μm to about 10 μm.

12. A pharmaceutical composition comprising the Crystalline Form B of claim 1 and a pharmaceutically acceptable excipient.

13. The Crystalline Form C of claim 1, wherein the X-ray powder diffraction pattern further comprises characteristic peaks expressed in values of degrees 2Θ at about 17.4±0.2, about 20.3±0.2, about 20.6±0.2, about 20.7±0.2 and about 21.2±0.2.

14. The Crystalline Form C of claim 1, which exhibits:
a thermogravimetric analysis thermogram substantially similar to FIG. 8
a differential scanning calorimetry thermogram having peak characteristics value at about 126.7±0.2 and about 151.5±0.2° C.; or
a differential scanning calorimetry thermogram pattern substantially similar to FIG. 7.

15. The Crystalline Form C of claim 1 with a polymorphic purity of at least about 50%.

16. The Crystalline Form C of claim 1, having a $D_{90}$ ranging from about 5 μm to about 10 μm.

17. A pharmaceutical composition comprising the Crystalline Form C of claim 1 and a pharmaceutically acceptable excipient.

18. An amorphous form of a Compound I-MsOH which exhibits a modulated DSC thermogram comprising a glass transition temperature at about 81.9° C.

19. A pharmaceutical composition comprising the amorphous form of claim 18 and a pharmaceutically acceptable excipient.

20. A method of making Crystalline Form A of Compound I-MsOH of claim 1, comprising:
(a) suspending a Compound I-MsOH in a suitable solvent to form a slurry and
(b) isolating Crystalline Form A of Compound I-MsOH.

21. The method of claim 20, wherein the Compound I-MsOH in step (a) comprises amorphous Compound I-MsOH.

22. The method of claim 20, wherein the suspending is at about 5° C. and the solvent is selected from the group consisting of ethyl acetate, isopropyl acetate, methyl isobutyl ketone, isopropanol, ethanol, 2-methyl-1-propanol, propyl acetate, acetonitrile, 1,2-dimethoxyethane, nitromethane, ethyl acetate/acetonitrile (50/50); ethyl acetate/acetonitrile/water (47.5/47.5/5); ethyl acetate/acetonitrile/pyridine (47.5/47.5/5); ethyl acetate/acetonitrile/dichloromethane (47.5/47.5/5); acetonitrile/ethyl acetate (95/5); acetonitrile/pyridine (95/5) and acetonitrile/dichloromethane (95/5).

23. The method of claim 20, wherein the suspending step (a) is conducted at a temperature of about 50° C. and the solvent is selected from the group consisting of ethyl acetate, isopropyl acetate, methyl isobutyl ketone, isopropanol, ethanol, 2-methyl-1-propanol, propyl acetate, acetonitrile, 1,2-dimethoxyethane, nitromethane, ethyl acetate/acetonitrile (50/50); ethyl acetate/acetonitrile/water (47.5/47.5/5); ethyl acetate/acetonitrile/pyridine (47.5/47.5/5); ethyl acetate/acetonitrile/dichloromethane (47.5/47.5/5); acetonitrile/ethyl acetate (95/5); acetonitrile/pyridine (95/5) and acetonitrile/dichloromethane (95/5).

24. A method of making Crystalline Form A of Compound I-MsOH of claim 1, comprising:
(a) suspending a Compound I-MsOH in a suitable solvent at a temperature of about 5° C.;
(b) heating the suspension of step (a) to a temperature of about 50° C.;
(c) isolating Crystalline Form A of Compound I-MsOH; and
(d) drying the isolated product under vacuum, and breaking up product to dry at about 40° C.;
or comprising:
(i) suspending a Compound I-MsOH in a suitable solvent at a temperature of about 25° C.;

(ii) heating the suspension of step (a) to a temperature of about 50° C.;
(iii) isolating Crystalline Form A of Compound I-MsOH; and
(iv) drying the isolated product under vacuum, and breaking up product to dry at about 40° C.;
or comprising:
(1) adding an anti-solvent to a solution of a Compound I-MsOH in a suitable solvent to precipitate Crystalline Form A; and
(2) isolating Crystalline Form A of Compound I-MsOH;
or comprising:
(A) adding an anti-solvent to a solution of a Compound I-MsOH in a suitable solvent to form an oil that converts to Crystalline Form A; and
(B) isolating Crystalline Form A of Compound I-MsOH;
or comprising:
(I) dissolving a Compound I-MsOH in a suitable solvent;
(II) evaporating a portion of the suitable solvent from the solution of step (I); and
(III) isolating Crystalline Form A of Compound I-MsOH;
or comprising:
(α) suspending a Compound I-MsOH in a suitable solvent;
(β) milling the suspension of step (α); and
(γ) isolating Crystalline Form A of Compound I-MsOH.

25. The method of claim 24, wherein the Compound I-MsOH in step (a), step (i), step (1), step (A), step (I), or step (a) comprises amorphous Compound I-MsOH.

26. The method of claim 24, wherein:
the suitable solvent in step (a) or step (i) is selected from the group consisting of ethyl acetate, isopropyl acetate, methyl isobutyl ketone, isopropanol, methyl ethyl ketone, acetone, 2-methyl-1-propanol, tert-butyl methyl ether, anisole, toluene, tetrahydrofuran, acetonitrile, 1,2-dimethoxyethane, nitromethane, ethyl acetate/acetonitrile (50/50); ethyl acetate/acetonitrile/pyridine (47.5/47.5/5); ethyl acetate/acetonitrile/dichloromethane (47.5/47.5/5); acetonitrile/ethyl acetate (95/5); acetonitrile/pyridine (95/5) and acetonitrile/dichloromethane (95/5);
the suitable solvent in step (1) is methanol and the suitable anti-solvent in step (1) is tert-butyl methyl ether;
the suitable solvent in step (A) is ethanol:water (90:10); and the suitable anti-solvent in step (A) is tert-butyl methyl ether;
the suitable solvent in step (A) is ethyl acetate: acetonitrile:water (47.5:47.5:5); and the suitable anti-solvent in step (A) is tert-butyl methyl ether;
the suitable solvent in step (A) is methanol; and the suitable anti-solvent in step (A) is tert-butyl methyl ether; or
the suitable solvent in step (I) is selected from the group consisting of anisole, 2-methyl-1-propanol and isopropanol/water (90:10).

27. The method of claim 24, wherein a ball mill is used in the milling step (β) and the suitable solvent in step (α) is selected from the group consisting of isopropanol, acetone, ethanol, acetonitrile and nitromethane.

28. A method of making Crystalline Form B of Compound I-MsOH of claim 1, comprising:
(a) suspending Compound I-MsOH in a suitable solvent and
(b) forming a suspension of Crystalline Form B of Compound I-MsOH in the solvent;
or comprising:
(i) dissolving a Compound I-MsOH in a suitable solvent;
(ii) adding a suitable anti-solvent to the solution of step (i); and
(iii) forming a suspension of Crystalline Form B of Compound I-MsOH.

29. The method of claim 28, wherein the Compound I-MsOH in step (a) or step (i) comprises amorphous Compound I-MsOH.

30. The method of claim 28, wherein the forming of the suspension of Crystalline Form B of Compound I-MsOH in step (b) is:
at about 5° C. and the solvent is selected from the group consisting of methyl ethyl ketone, acetone and tetrahydrofuran; or
at about 25° C. and the solvent is selected from the group consisting of acetone and tetrahydrofuran; or
wherein the forming the suspension of Crystalline Form B of Compound I-MsOH in step (iii) is at about 5° C. or at about 25° C., the suitable solvent is dichloromethane and the suitable anti-solvent is n-heptane.

31. A method of making Crystalline Form C of Compound I-MsOH of claim 1, comprising:
(a) filtering suspension of Crystalline Form B of Compound I-MsOH, and
(b) drying the filtered product under vacuum, and breaking up product to dry at ambient conditions;
or comprising:
(i) filtering suspension of Crystalline Form B of Compound I-MsOH, and
(ii) drying the filtered product under vacuum, and breaking up product to dry at less than 20° C.;
or comprising:
(1) filtering suspension of Crystalline Form B of Compound I-MsOH, and
(2) drying the filtered product under vacuum, and breaking up product to freeze-dry.

32. A method of making an amorphous form of Compound I-MsOH of claim 18, comprising:
(a) dissolving a Compound I-MsOH in a suitable solvent;
(b) evaporating a portion of the suitable solvent from the solution of step (a); and
(c) isolating an amorphous form of Compound I-MsOH;
or comprising
(i) dissolving a Compound I-MsOH in a suitable solvent;
(ii) freeze-drying solution of step (a); and
(iii) isolating an amorphous form of Compound I-MsOH.

33. The method of claim 32, wherein:
the suitable solvent in step (a) is selected from the group consisting of dichloromethane, tetrahydrofuran and methanol;
the evaporating step (b) is conducted under ambient conditions the evaporating step (b) is conducted under pressure below that of atmospheric pressure;
or
the suitable solvent in step (i) is a mixture of tert-butanol and water.

34. The Crystalline Form A of Compound I-MsOH produced by the method of 44.

35. The Crystalline Form B of Compound I-MsOH produced by the method of 65.

36. The Crystalline Form C of Compound I-MsOH produced by the method of 72.

37. The amorphous form of Compound I-MsOH produced by the method of 75.

38. A method of treating fibrosis or a fibrotic disease or condition in a subject in need thereof, comprising administering a therapeutically effective amount of the Crystalline Form A of Compound I-MsOH of claim 1.

39. A method of treating fibrosis or a fibrotic disease or condition in a subject in need thereof, comprising administering a therapeutically effective amount of the Crystalline Form B of Compound I-MsOH of claim 1.

40. A method of treating fibrosis or a fibrotic disease or condition in a subject in need thereof, comprising administering a therapeutically effective amount of the Crystalline Form C of Compound I-MsOH of claim 1.

41. A method of treating fibrosis or a fibrotic disease or condition in a subject in need thereof, comprising administering a therapeutically effective amount of the amorphous form of Compound I-MsOH according to claim 18.

42. The method of claim 38, wherein the fibrosis or fibrotic disease or condition is liver fibrosis or renal fibrosis.

43. The method of claim 42, wherein the liver fibrosis is associated with non-alcoholic steatohepatitis (NASH) or non-alcoholic fatty liver disease (NAFLD).

44. The Crystalline Form A of Compound I-MsOH produced by the method of claim 24.

* * * * *